United States Patent
Kroll et al.

(10) Patent No.: US 10,118,031 B2
(45) Date of Patent: Nov. 6, 2018

(54) METHOD AND APPARATUS FOR IMPLANTABLE CARDIAC LEAD INTEGRITY ANALYSIS

(71) Applicant: Lambda Nu Technology LLC, Orono, MN (US)

(72) Inventors: Mark Kroll, Crystal Bay, MN (US); Charles Swerdlow, Los Angeles, CA (US); Daniel T. Kollmann, Andover, MN (US)

(73) Assignee: Lambda Nu Technology LLC, Orono, MN (US)

( * ) Notice: Subject to any disclaimer, the term of this patent is extended or adjusted under 35 U.S.C. 154(b) by 382 days.

(21) Appl. No.: 14/203,688

(22) Filed: Mar. 11, 2014

(65) Prior Publication Data

US 2015/0005862 A1 Jan. 1, 2015

Related U.S. Application Data

(60) Provisional application No. 61/841,107, filed on Jun. 28, 2013.

(51) Int. Cl.
*A61N 1/00* (2006.01)
*A61N 1/05* (2006.01)
*A61N 1/08* (2006.01)

(52) U.S. Cl.
CPC ............ *A61N 1/0563* (2013.01); *A61N 1/08* (2013.01); *A61N 2001/083* (2013.01)

(58) Field of Classification Search
CPC ........ A61N 1/37; A61N 1/3962; A61N 1/056; A61N 1/3706; A61N 1/3621; A61N 2001/083
USPC .................................................. 607/4, 122
See application file for complete search history.

(56) References Cited

U.S. PATENT DOCUMENTS

| | | | |
|---|---|---|---|
| 3,599,055 A | 8/1971 | Bloom | |
| 4,766,549 A | 8/1988 | Schweitzer, III et al. | |
| 5,003,975 A | 4/1991 | Hafelfinger et al. | |
| 5,231,987 A | 8/1993 | Robson | |
| 5,243,980 A | 9/1993 | Mehra | |

(Continued)

FOREIGN PATENT DOCUMENTS

| | | |
|---|---|---|
| EP | 0288630 B1 | 11/1988 |
| EP | 2032027 B1 | 10/2011 |

OTHER PUBLICATIONS

"Agilent Impedance Measurement Handbook A Guide to Measurement Technology and Techniques 4th Edition," Agilent Technologies, Inc., Jun. 17, 2009, 140 pages.

(Continued)

*Primary Examiner* — Eric D. Bertram
*Assistant Examiner* — Elizabeth K So
(74) *Attorney, Agent, or Firm* — Patterson Thuente Pedersen, P.A.

(57) ABSTRACT

Scientific and medical system circuitry for diagnosis of implantable cardioverter defibrillator (ICD) lead conductor anomalies, in particular conductor migration and externalization within an ICD implantable cardiac lead. The system determines an "imaginary" component of the high frequency transmission line impedance having certain spectral changes that correspond to radially outward movements or local externalization of a conductor within a lead body allowing for the detection of conductor migration and small insulation failures.

10 Claims, 58 Drawing Sheets

(56) References Cited

U.S. PATENT DOCUMENTS

| | | | |
|---|---|---|---|
| 5,361,776 A | 11/1994 | Samuelson et al. | |
| 5,405,363 A | 4/1995 | Kroll et al. | |
| 5,453,698 A | 9/1995 | Williams et al. | |
| 5,557,210 A | 9/1996 | Cappa et al. | |
| 5,741,311 A | 4/1998 | McVenes et al. | |
| 5,755,742 A | 5/1998 | Schuelke et al. | |
| 5,897,577 A | 4/1999 | Cinbis et al. | |
| 5,944,746 A | 8/1999 | Kroll | |
| 6,104,954 A | 8/2000 | Blunsden | |
| 6,317,633 B1 | 11/2001 | Jorgenson et al. | |
| 6,415,179 B1 | 7/2002 | Pendekanti et al. | |
| 6,445,951 B1 | 9/2002 | Mouchawar | |
| 6,490,486 B1 | 12/2002 | Bradley | |
| 6,580,948 B2 | 6/2003 | Haupert et al. | |
| 6,928,325 B2 | 8/2005 | Zhu et al. | |
| 7,047,083 B2 | 5/2006 | Gunderson et al. | |
| 7,081,130 B2 | 7/2006 | Jang | |
| 7,120,563 B2 | 10/2006 | Bechhoefer et al. | |
| 7,289,851 B2 | 10/2007 | Gunderson et al. | |
| 7,369,893 B2 | 5/2008 | Gunderson | |
| 7,454,249 B1 | 11/2008 | Bornzin et al. | |
| 7,623,919 B2 | 11/2009 | Goetz et al. | |
| 7,747,320 B1 | 6/2010 | Kroll et al. | |
| 7,764,998 B1 | 7/2010 | Raddatz | |
| 8,200,330 B2 | 6/2012 | Kroll et al. | |
| 8,352,033 B2 | 1/2013 | Kroll | |
| 8,457,742 B2 | 6/2013 | Jacobson | |
| 8,463,382 B2 | 6/2013 | Jorgenson et al. | |
| 8,463,384 B2 | 6/2013 | Germanson et al. | |
| 8,467,872 B2 | 6/2013 | Hareland | |
| 8,498,706 B2 | 7/2013 | Pei et al. | |
| 8,577,457 B2 | 11/2013 | Miller et al. | |
| 8,644,932 B2 | 2/2014 | Seifert et al. | |
| 8,682,436 B2 | 3/2014 | Ghosh et al. | |
| 8,700,156 B2 | 4/2014 | Kroll | |
| 8,812,103 B2 | 8/2014 | Kroll et al. | |
| 8,825,158 B2 | 9/2014 | Swerdlow | |
| 9,272,150 B2 | 3/2016 | Kroll et al. | |
| 9,427,577 B2 | 8/2016 | Kroll et al. | |
| 9,486,624 B2 | 11/2016 | Swerdlow | |
| 9,675,799 B2 | 6/2017 | Kroll et al. | |
| 9,814,876 B2 | 11/2017 | Swerdlow | |
| 9,821,156 B2 | 11/2017 | Kroll et al. | |
| 9,827,416 B2 | 11/2017 | Swerdlow | |
| 2003/0004552 A1 | 1/2003 | Plombon et al. | |
| 2003/0036772 A1 | 2/2003 | Saphon et al. | |
| 2004/0010303 A1 | 1/2004 | Bolea et al. | |
| 2004/0068301 A1 | 4/2004 | Waltman et al. | |
| 2004/0158290 A1 | 8/2004 | Girouard et al. | |
| 2004/0230385 A1* | 11/2004 | Bechhoefer | G01R 31/11 702/57 |
| 2005/0137636 A1 | 6/2005 | Gunderson et al. | |
| 2005/0187586 A1 | 8/2005 | David et al. | |
| 2005/0256547 A1 | 11/2005 | Stahmann et al. | |
| 2006/0025828 A1 | 2/2006 | Armstrong et al. | |
| 2006/0116747 A1 | 6/2006 | Eick et al. | |
| 2006/0135886 A1 | 6/2006 | Lippert et al. | |
| 2006/0241513 A1 | 10/2006 | Hatlestad | |
| 2006/0265038 A1 | 11/2006 | Hagen et al. | |
| 2007/0208387 A1 | 9/2007 | Mower | |
| 2008/0208271 A1 | 8/2008 | Sih et al. | |
| 2008/0309351 A1 | 12/2008 | Stewart et al. | |
| 2009/0099615 A1 | 4/2009 | Kroll | |
| 2009/0270938 A1 | 10/2009 | Pei et al. | |
| 2009/0292331 A1 | 11/2009 | Gunderson et al. | |
| 2009/0299431 A1 | 12/2009 | Schecter | |
| 2009/0299432 A1 | 12/2009 | Stadler et al. | |
| 2009/0306735 A1 | 12/2009 | Lagercrantz et al. | |
| 2010/0179446 A1 | 7/2010 | Bojovic et al. | |
| 2010/0179538 A1* | 7/2010 | Podhajsky | A61B 18/1206 606/35 |
| 2010/0204758 A1 | 8/2010 | Boon et al. | |
| 2010/0228307 A1 | 9/2010 | Kroll et al. | |
| 2010/0324629 A1 | 12/2010 | Jorgenson et al. | |
| 2011/0054554 A1* | 3/2011 | Swerdlow | A61N 1/3706 607/5 |
| 2011/0054556 A1 | 3/2011 | Swerdlow | |
| 2011/0054558 A1 | 3/2011 | Gunderson et al. | |
| 2011/0160808 A1 | 6/2011 | Lyden et al. | |
| 2011/0160829 A1 | 6/2011 | Foster et al. | |
| 2011/0230741 A1* | 9/2011 | Liang | A61B 5/14532 600/347 |
| 2012/0035491 A1 | 2/2012 | Mahajan et al. | |
| 2012/0191153 A1 | 7/2012 | Swerdlow et al. | |
| 2012/0197331 A1 | 8/2012 | Germanson et al. | |
| 2012/0197365 A1 | 8/2012 | Germanson et al. | |
| 2013/0013038 A1 | 1/2013 | Miller | |
| 2013/0030496 A1 | 1/2013 | Karamanoglu et al. | |
| 2013/0123871 A1 | 5/2013 | Kroll | |
| 2013/0165986 A1 | 6/2013 | Ghosh et al. | |
| 2013/0304139 A1 | 11/2013 | Musley et al. | |
| 2013/0304160 A1 | 11/2013 | Gunderson et al. | |
| 2013/0325079 A1 | 12/2013 | Kroll et al. | |
| 2013/0325080 A1 | 12/2013 | Kroll et al. | |
| 2014/0155947 A1 | 6/2014 | Kroll et al. | |
| 2014/0324123 A1 | 10/2014 | Kroll et al. | |
| 2014/0371831 A1 | 12/2014 | Swerdlow | |
| 2015/0088213 A1 | 3/2015 | Swerdlow | |
| 2015/0151118 A1 | 6/2015 | Kroll et al. | |
| 2015/0273225 A1 | 10/2015 | Swerdlow et al. | |
| 2016/0250462 A1 | 9/2016 | Kroll et al. | |
| 2016/0271390 A1 | 9/2016 | Kroll et al. | |
| 2016/0375239 A1 | 12/2016 | Swerdlow | |
| 2017/0120045 A1 | 5/2017 | Swerdlow | |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Lo et al., "Noise-Domain Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

(56) References Cited

OTHER PUBLICATIONS

Oral, Hakan et al., "Pulmonary Vein Isolation for Paroxysmal and Persistent Atrial Fibrillation," Circulation, 2002, pp. 1077-1081.
Pappone, Carlo, "Pulmonary Vein Denervation Enhances Long-Term Benefit After Circumferential Ablation for Paroxysmal Atrial Fibrillation," Circulation, 2004, pp. 327-334.
Patterson, E. et al., "Triggered Firing in Pulmonary Veins Initiated by In Vitro autonomic nerve stimulation," Heart Rhythm, 2005, pp. 624-631.
Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.
Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.
Po, Sunny S. et al., "Experimental Model for Paroxysmal Atrial Fibrillation Arising at the Pulmonary Vein-Atrial Junctions," Heart Rhythm, 2006, pp. 201-208.
Randall, David C., et al., "Ablation of Posterior Atrial Ganglionated Plexus Potentiates Sympathetic Tachycardia to Behavioral Stress," Comp. Physiol., 1998, pp. 779-787.
Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.
Schauerte, Patrick et al., "Catheter Ablation of Cardiac Autonomic Nerves for Prevention of Vagal Atrial Fibrillation," Circulation, 2000, pp. 2774-2780.
Schauerte, Patrick, "Focal Atrial Fibrillation: Experimental Evidence for a Pathophysiologic Role of the Autonomic Nervous System," Cardiovasc. Electrophysiol., 2001, pp. 592-599.
Scherlag, Benjamin J., et al., "Autonomically Induced Conversion of Pulmonary Vein Focal Firing Into Atrial Fibrillation," J. Am Coll. Cardiol., 2005, pp. 1878-1886.
Scherlag, Benjamin, "Electrical Stimulation to Identify Neural Elements on the Heart: Their Role in Atrial Fibrillation," J. Interv. Card, Electrophysiol, 2005, pp. 37-42.
Tai, C., "Stimulation Analysis of Conduction Block in Unmyelinated Axons Induced by High-Frequency Biphasic Electrical Currents," IEEE T-BME, 2005, p. 1323.
Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.
Tomasic, "Acute and Chronic High-Frequency Properties of Cardiac Pacing and Defibrillation Leads," Med Biol Eng Comput 50:827-837, 2012.
Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.

Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.
Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.
Application and File history for U.S. Appl. No. 12/868,056, filed Aug. 25, 2010, now U.S. Pat. No. 8,825,158. Inventor Swerdlow.
Application and File history for U.S. Appl. No. 13/735,599, filed Jan. 7, 2013, now U.S. Pat. No. 8,700,156. Inventor Kroll.
Application and File history for U.S. Appl. No. 13/842,838, filed Mar. 15, 2013. Inventor Kroll.
Application and File history for U.S. Appl. No. 12/252,310, filed Oct. 15, 2008, now U.S. Pat. No. 8,352,033. Inventor: Kroll.
Application and File history for U.S. Appl. No. 13/843,145, filed Mar. 15, 2013, now U.S. Pat. No. 8,812,103. Inventors: Kroll et al.
Application and File history for U.S. Appl. No. 13/833,477, filed Mar. 15, 2013. Inventors: Kroll et al.
Application and File history for U.S. Appl. No. 14/224,876, filed Mar. 25, 2014. Inventors: Kroll et al.
Application and File history for U.S. Appl. No. 14/224,281, filed Mar. 25, 2014. Inventors: Kroll et al.
Application and File history for U.S. Appl. No. 14/224,335, filed Mar. 25, 2014. Inventors: Kroll et al.
Application and File history for U.S. Appl. No. 14/453,679, filed Aug. 7, 2014. Inventors: Kroll et al.
Application and File history for U.S. Appl. No. 14/472,027, filed Aug. 28, 2014. Inventors: Kroll et al.
PCT Application No. PCT/US2013/043386, filed May 30, 2013, Search Report and Written Opinion dated Sep. 27, 2013, 10 pages.
PCT Application No. PCT/US2013/043389, filed May 30, 2013, Search Report and Written Opinion dated Sep. 5, 2013, 9 pages.
PCT Application No. PCT/US2013/072957, Filed Dec. 4, 2013, Search Report and Written Opinion dated Mar. 6, 2014.
PCT Application No. PCT/US2015/022435, Filed Mar. 25, 2015, Search Report and Written Opinion dated Jun. 29, 2015.
EP Application No. 13796833.5, Extended EP Search Report dated Feb. 11, 2016, 9 pages.
European Extended Search Report; EP Application No. 13859688.7, dated May 27, 2016, 11 pages.
Application and File history for U.S. Appl. No. 15/054,538, filed Feb. 26, 2016. Inventors: Kroll et al.
Application and File history for U.S. Appl. No. 15/080,343, filed Mar. 24, 2016. Inventors: Kroll et al.
Application and File history for U.S. Appl. No. 15/344,864, filed Nov. 7, 2016. Inventors: Swerdlow.
Application and File history for U.S. Appl. No. 15/013,201, filed Feb. 4, 2016. Inventors: Swerdlow.
Application and File history for U.S. Appl. No. 15/810,324, filed Nov. 13, 2017. Inventors: Swerdlow.
Application and File history for U.S. Appl. No. 15/356,962, filed Nov. 21, 2016. Inventors: Kroll.

* cited by examiner

| Lead Name | Serial Number | Model | Externalized wire distance from tip (cm) |
|---|---|---|---|
| Lead 10 | AEJ12002 | 7071/65 | 9 (RVC)  18 (ring) |
| Lead 11 | ABP10398 | 7041/65 | 9 |
| Lead 12 | ABP15141 | 7041/65 | 18 |
| Lead 13 | ABL24022 | 7040/65 | 9 |
| Lead 14 | ABP15170 | 7041/65 | 18 |

Fig. 20

| Lead | Normal Min Z Imag | Exposed Min Z Imag | NSD above mean Normal |
|---|---|---|---|
| 10 | -266.8 | -238.0 | 4.36 |
| 11 | -280.3 | -185.2 | 10.44 |
| 12 | -265.9 | -172.6 | 11.90 |
| 13 | -283.1 | -207.9 | 7.82 |
| 14 | -282.8 | -200.7 | 8.65 |
| Mean | -275.8 | | |
| StDev | 8.7 | | |

Fig. 42

| Lead Name | Serial Number | Model | Externalized wire distance from tip (cm) |
|---|---|---|---|
| Lead 10 | AEJ12002 | 7071/65 | 9 (RVC), 18 (ring) |
| Lead 11 | ABP10398 | 7041/65 | 9 |
| Lead 12 | ABP15141 | 7041/65 | 18 |
| Lead 13 | ABL24022 | 7040/65 | 9 |
| Lead 14 | ABP15170 | 7041/65 | 18 |

Fig. 43

METHOD AND APPARATUS FOR IMPLANTABLE CARDIAC LEAD INTEGRITY ANALYSIS

RELATED APPLICATION

The present application claims the benefit of U.S. Provisional Application No. 61/841,107 filed Jun. 28, 2013, which is incorporated herein in its entirety by reference.

FIELD OF THE INVENTION

The present invention relates generally to electrical therapeutic systems for applying electrical therapy to patients for detecting and/or treating cardiac arrhythmias. More particularly, the invention relates to a method and apparatus for analyzing implantable cardiac leads to promote patient safety by evaluating possible issues with implantable cardiac lead integrity, including partial insulation failures, conductor migration, and/or externalization of conductors in multilumen leads.

BACKGROUND

Implantable cardioverter defibrillators (ICDs) are used to provide various types of therapy to treat cardiac arrhythmias in a patient, including, for example defibrillation. These devices typically consist of a hermetic housing implanted into a patient and connected to at least one defibrillation electrode. The housing of the ICD contains electronic circuitry for monitoring the condition of the patient's heart, usually through sensing electrodes, and also contains the battery, high voltage circuitry and control circuitry to generate, control and deliver defibrillation shocks. Typically, one or more of the defibrillation electrodes are connected to circuitry within the ICD via one or more implantable cardiac leads that extend from the housing to the defibrillation electrodes. The housing of the ICD may also include one or more defibrillation electrodes configured on the exterior of the housing.

Implantable transvenous ICD leads are generally elongated lead bodies made of biocompatible insulation material(s) including multiple parallel lumens with each lumen carrying one or more conductors that run between connectors on a proximal end to electrodes proximate a distal portion of the implantable cardiac lead. The number of conductors required for true-bipolar ICD implantable cardiac leads is typically four (two conductors for sensing and pacing that provide conduction paths for a lower power sensed signal and a ground return, and two conductors for therapy that provide conduction paths for higher power defibrillation shocks, a therapy signal and a ground return). Integrated-bipolar leads can combine one defibrillation electrode as a pace-sense electrode and thus have only three conductors. In addition, a separate center inner coil and stylet lumen may be provided for use in implanting the ICD implantable cardiac lead. The center inner coils may also include conductors that carry electric signals to pacing sense/therapy electrodes. The diameter of the implantable cardiac lead body must be small enough to navigate the blood vessels through which the implantable cardiac lead is implanted, while still being robust enough to maintain electrical and mechanical integrity over the course of bending and movement during hundreds of thousands of heart beats and respirations.

The long-term reliability and safety of implantable cardiac leads is a significant issue. Conductor anomalies in the implantable cardiac leads for ICDs can result in morbidity and/or mortality from loss of pacing, inappropriate ICD shocks, and/or ineffective treatment of ventricular tachycardia or ventricular fibrillation. The early diagnosis of conductor anomalies for implantable cardiac leads is a critically important step in reducing these issues and making ICDs safer.

One particular conductor anomaly that is unique to implantable cardiac leads occurs when a conductor migrates through the soft silicone material of the implantable cardiac lead body away from the original position of the conductor within a lumen. This problem was originally described for St. Jude's recalled Riata™ and Riata ST™ leads, and they are considered as illustrative examples. In some cases, the cable including the conductor may abrade against the lumen that constrains it to migrate outwardly within the silicone implantable cardiac lead body ("inside-out" abrasion) without breaking through the external insulating layer of the implantable cardiac lead body. In other cases, the conductor may continue to abrade against the silicone elastomer lead body until it breaks through the surface and become externalized and exposed to body fluids and tissue. At this stage, it may be detected by fluoroscopy. Initially, the thin polymer (ETFE) insulating layer surrounding the cable remains intact, at least without delivery of high-voltage shocks. Over time, this ETFE secondary insulating layer can, on rare occasions, become abraded or damaged due to one of various mechanisms. Exposed conductors can also result in sensing of non-physiological electrical signals, "noise", if the exposed conductor is connected to a sensing electrode. This results in incorrect detection of ventricular tachycardia or fibrillation (over-sensing) that may result in unnecessary painful shocks. Even more worrisome, this problem may result in failed defibrillation shocks if the conductor is connected to the primary (distal) shock coil located in the right ventricle (RV). In this case, the patient will likely die of the arrhythmia unless promptly defibrillated by an external defibrillator. Failed defibrillation shocks are particularly likely if the conductor to the RV shock coil abrades against the proximal shock coil in the superior vena cava (SVC) resulting in a short circuit when a shock is needed. Such "under-the-coil" abrasions may occur without exteriorized cables so that they are undetectable by fluoroscopy, hence only detected when a shock is delivered. It is not known how often or the extent to which early-stage failures of outer insulation may compromise sensing and/or defibrillation.

Further, exteriorized cables are not helpful in identifying inside-out abrasions occurring in Riata ST Optim™ and similar Durata™ leads. These leads are designed similarly to the Riata and Riata ST have an additional, abrasion-resistant coating of silicone-polyurethane copolymer (Optim™) tubing on the external surface. Intact, external tubing prevents cables that have abraded through their lumens from exteriorizing, but it does not alter the fundamental process of "inside-out" abrasion. Under the shock-coils, coated leads are identical to similarly-designed leads without tubing, and they provide no additional protection against inside-out, cable-coil abrasion. Presently, there is no way to detect inside-out abrasions in coated leads unless an electrical abnormality resulting in lead failure occurs.

Numerous approaches have been suggested for trying to diagnosis and correct for the problems of implantable cardiac lead failures and anomalies. Most involve the classic approach of subjecting the implantable cardiac lead to a periodic test pulse, measuring the direct-current impedance of the test pulse and then comparing that impedance to an expected range of acceptable impedance values. In implantable cardiac leads, however, only one end of the conductor is generally accessible for testing purposes and changes in system impedance may be dominated by changes unrelated to conductor or implantable cardiac lead faults. For example, the reference impedance for pace-sense conductors is in the range of about 15-50Ω, and usually is constant within about 10% for an individual conductor. But the reference impedance for the combined electrode-tissue interface and connected body tissue ranges from about 300Ω to greater than 1000Ω. More importantly, biological variations of up to 300Ω are common, and variations of greater than 1000Ω may occur without conductor or insulation failures. The impact of these normal impedance variations on traditional impedance-based implantable cardiac lead integrity testing is only now being understood as discussed, for example, in a paper by one of the inventors (Swerdlow, *JACC*, 2011).

Other potential solutions to address these problem in the sensing and detection process of the implantable device have been suggested in papers by one of the inventors, either by increasing the number of interval counts (NIC) used by the detection algorithm (Swerdlow, Circulation, 2008), or by using a sensing integrity counter (SIC) to monitor high numbers of possible over-sensing events (Gunderson, *Heart Rhythm Society*, 2010). The results of testing an improved implantable cardiac lead integrity algorithm (LIA) based on a combination of abnormally high impedance and over-sensing of non-sustained tachycardias are reported in (Swerdlow, *Circulation* 2010). Published patent applications and patents by the inventors have described other approaches for addressing these problems, e.g., U.S. Pat. Nos. 7,747,320, 8,200,330, 8,352,033, 8,798,750, and 8,825,158.

Unfortunately, none of these approaches provide a good solution for the unique problems of diagnosis and analysis of conductor anomalies due to migration and/or externalization. At present, there is no testing available to determine if the conductors are migrating in the implantable cardiac lead body as there is no "ohmic" short or parasitic pathway. Even when the conductors have become externalized and potentially abraded, it is not possible to detect this insulation failure as the small parasitic conduction through the insulation break is swamped by minor variations in the higher resistance of the measured current path including one or more defibrillation electrode coils or the pace-sense electrodes. And, over-estimating the potential for implantable cardiac lead conductor anomalies has its own negative consequences, as a false positive may result in an unnecessary implantable cardiac lead replacement surgery, with corresponding expense and risk.

What is desired are method and apparatus that could analyze and identify implantable cardiac lead conductor anomalies at the subclinical stage, before they present as a clinical problem, and do so with a high sensitivity and specificity that minimizes false positives for implantable cardiac lead conductor anomalies.

SUMMARY OF THE INVENTION

Embodiments of the present invention provide methods and apparatus for analyzing implantable cardiac leads to promote patient safety by evaluating possible issues with implantable cardiac lead integrity, including conductor migration and/or externalization. Instead of a classic impedance-based integrity test, an "imaginary" component of a high frequency transmission line impedance test having certain spectral changes, that correspond to movements of the conductor in relation to the outer insulation, is utilized to diagnose potential implantable cardiac lead integrity issues. This "imaginary impedance" test allows for the detection and identification of conductor migration and small insulation failures in implantable cardiac leads.

In one embodiment, a method of detecting conductor migration and/or externalization within an implantable cardiac lead includes the steps of determining an implantable cardiac lead length, calculating a test frequency based on the implantable cardiac lead length, applying a frequency signal source to the implantable cardiac lead, wherein the frequencies are within 10% of the test frequency, measuring an imaginary component of a transmission line impedance of the implantable cardiac lead, and determining whether the imaginary impedance increased approximately 90% or greater at the test frequency. If so, the method can further include additional evaluation and indication of a detection of a potential conductor migration and/or small insulation failures in an implantable cardiac lead.

In another embodiment, a method of detecting conductor migration and/or externalization within an implantable cardiac lead includes applying a high-frequency signal source to an implantable cardiac lead, the signal source providing frequencies of 100 MHz or higher to the implantable cardiac lead, measuring an imaginary component of a transmission line impedance of the implantable cardiac lead, and determining whether the imaginary impedance increased at frequencies in the range of 150 MHz to 250 MHz. A further aspect of this embodiment can include determining a highest frequency of imaginary impedance increase and estimating a location of externalization by calculating a one-quarter wavelength from the implantable cardiac lead end. Again, this method can further include additional evaluation and indication of a detection of a potential conductor migration and/or small insulation failures in an implantable cardiac lead.

In another embodiment, a method of detecting conductor migration and/or externalization within an implantable cardiac lead comprises applying a frequency signal source to an implantable cardiac lead, the signal source providing frequencies of 100 MHz or higher to the implantable cardiac lead, measuring an imaginary component of a transmission line impedance of the implantable cardiac lead during a frequency sweep of 100 MHz to 200 MHz, and determining a decrease in the peak imaginary impedance to 217Ω or less. Again, this method can further include additional evaluation and indication of a detection of a potential conductor migration and/or small insulation failures in an implantable cardiac lead.

In another embodiment, an apparatus for detecting conductor migration and/or externalization within an implantable cardiac lead comprises an implantable lead tester housed within the ICD. A microcontroller with analog I/O controls the implantable lead tester. The circuitry for the implantable lead tester can include the microcontroller feeding at least one voltage-controlled oscillator which in turn feeds at least one input of a high-frequency multiplier thus providing a squaring function. The signal is then fed to a DC blocking capacitor resulting in a doubling of the frequency. This frequency, as a "carrier" signal is fed into a Quadrature Demodulator (QD). A sense resistor is provided a current (as a voltage drop) that is fed from the resistor to the QD as the RF signal. Outputs of the QD are then fed back to the microcontroller as $I_{REAL}$ and $I_{IM}$. The sensed current is isolated, rectified and smoothed with a diode, resistor and capacitor and fed back to the microcontroller as $I_{RECT}$ as is the VCO voltage with a separate diode, resistor and capacitor and fed back as $V_{RECT}$. Using the inputs, the microcontroller can then calculate the real and imaginary impedances.

In another embodiment, the ICD circuitry comprises an energy storage capacitor and an H-bridge. The H-bridge can be provided with a number of switches. The output of this configuration drives the RV coil cable. A feed-thru capacitor is provided to block RF interference. A MOSFET is provided between the feed-thru capacitor and ground with the lead tester inserted between the output of the feed-thru capacitor and the gate of the MOSFET. In one embodiment the ICD circuitry can be included as part of the ICD while in other embodiments, it can be external to the ICD.

Systems for automatically, semi-automatically or manually initiating the various embodiments of the present invention can be provided as part of circuitry and/or software within an implantable device, as part of a diagnostic device, or any combination thereof.

Another significant advantage of various embodiments of the present invention is the ability to more accurately measure impedance without affecting the heart due to the very high frequency nature of the test signals.

BRIEF DESCRIPTION OF THE DRAWINGS

The invention may be more completely understood in consideration of the following detailed description of various embodiments of the invention in connection with the accompanying drawings, in which:

FIG. 20 illustrates a table that details the lead name, lead serial number, model number, and the distance from tip where the externalization was introduced on the RV coil conductor during testing.

FIG. 42 illustrates the testing results for swept frequencies from 100 MHz to 200 MHz for the RV coil conductor $Z_{imag}$ for an exposed conductor.

FIG. 43 illustrates a table that details the lead name, lead serial number, model number, and the distance from tip where the externalization was introduced on the ring conductor during testing.

Figure 1:
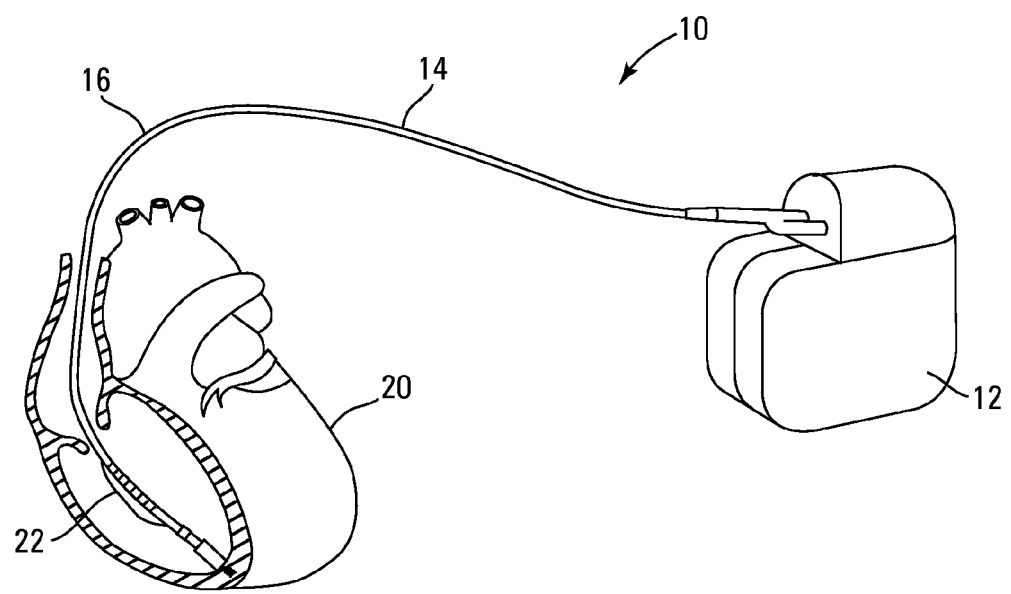
FIG. 1 depicts an ICD pulse generator connected to a patient's heart via a transvenous implantable cardiac lead used for pacing and defibrillation, the implantable cardiac lead having an externalized conductor within a chamber of the heart.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The embodiments of the present invention provide methods and apparatus for analyzing implantable cardiac leads to promote patient safety by evaluating possible issues with lead integrity, including conductor migration and/or externalization. The embodiments use an "imaginary" component of a high frequency transmission line impedance test having certain spectral changes that correspond to movements of the conductor to diagnose potential implantable cardiac lead integrity issues. This "imaginary impedance" test allows for the detection and identification of conductor migration and small insulation failures in implantable cardiac leads.

One application applies to diagnosis of conductor anomalies in implantable cardiac leads attached to an implantable medical device with a pulse generator, such as an ICD. Referring to FIG. 1, the implantable cardiac lead system 10 includes an implantable cardioverter defibrillator (ICD) pulse generator 12 and an implantable cardiac lead 14. The implantable cardiac lead 14 comprises an elongated lead body 16 enclosing conductors 22. In this application, the ICD 12 is implanted in the chest of a human patient, and the implantable cardiac lead 14 extends to the heart 20. The implantable cardiac lead 14 may be implanted intra-cardiac as shown, but may alternatively be deployed intravascularly or subcutaneously. Long term reliability and safety of implantable cardiac leads 14 is an issue and one particular conductor 22 anomaly, as is depicted in FIG. 1, occurs when a conductor 22 migrates to the limits of the implantable cardiac lead body 16, breaks through the implantable cardiac lead outer insulation and becomes externalized. In some instances, the insulation covering the externalized conductor 22 can abrade thus exposing the conductor 22 to body fluids and tissue.

Figure 2:
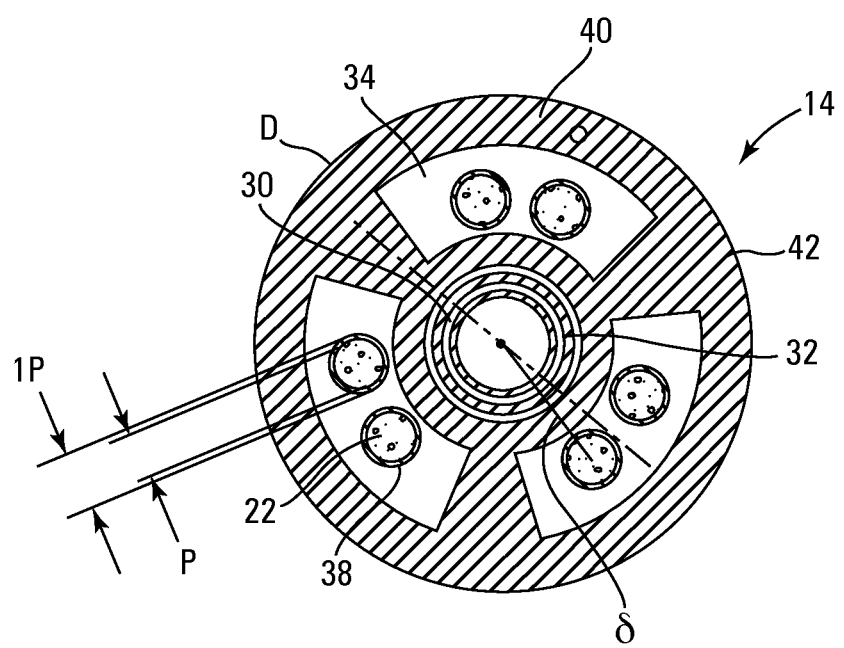
FIG. 2 is a cross-sectional view of a multi-lumen ICD implantable cardiac lead.

A cross-sectional view of a multi-lumen ICD implantable cardiac lead known to have a propensity for migration and/or externalization failures is illustrated in FIG. 2. The implantable cardiac lead 14 is comprised of a lumen and center inner coil 30 surrounded by PTFE insulation 32, a plurality of lumens 34 each containing a pair of conductors 22 with each conductor 22 surrounded by ETFE insulation 38, an outer insulating layer 40, and a silicone insulation 42 disposed between the inner coil PTFE insulation 32 and the outer insulating layer 40. The plurality of lumens 34 are disposed in the silicone insulation 42. The conductors 22 carry electric current to the anode pace/sense electrode, high voltage RV coil and high voltage SVC coil. The conductors 22 are known to migrate through the soft silicone insulation 42 and can break through the outer insulating layer 40 thus becoming externalized. While this cardiac lead 14 is described as an example of an implanted lead that may experience various lead failure or degradation issues, it will be recognized that the various embodiments of the present invention are not limited to this particular type of lead and may be applied more generally to a variety of implantable leads for cardiac nerve or tissue sensing and/or stimulation.

Disclosed is a method and apparatus for analyzing implantable cardiac leads to promote patient safety by allowing a practitioner to determine, inter alia, if a conductor 22 has migrated within the implantable cardiac lead 14, if the conductor 22 has breached the outer insulating layer 40 and become externalized, and/or if the conductor insulation 38 has been abraded or damaged. The method uses an "imaginary" component of the high frequency transmission line impedance having certain spectral changes that correspond to movements of the conductor 22, hereinafter referred to as "imaginary impedance". This "imaginary impedance" allows the detection of conductor 22 migration and small insulation 38 failures.

Referring to FIG. 2, depicting a cross-sectional view of a known multi-lumen implantable cardiac lead 14, the outer diameter D of the implantable cardiac lead 14 is about 2.08 mm. The conductor 22 diameter d is about 0.21 mm and including its ETFE insulation 38, the insulated conductor 22 diameter d1 is about 0.27 mm. The conductor 22 offset δ, which is the center of the implantable cardiac lead 14 to the center of the conductor 22, is about 0.64 mm.

It is known that the transmission line impedance (TLZ) of a coaxial cable is given by the standard formula:

$$Z_o = 60 \log_e(D/d)/\sqrt{k} \quad \text{(equation 1)}$$

where D is the outer diameter, d is the conductor diameter and κ is the relative permeability of the insulator compared to a vacuum. The relative permeability is about 3 for silicone and about 2.5 for ETFE. Thus, for a silicone implantable cardiac lead with the dimensional characteristics of the known implantable cardiac lead 14, assuming that the conductor 22 was centered within the implantable cardiac lead 14, the transmission line impedance simplifies to:

$$Z_o = 34.6 \log_e(D/d) \quad \text{(equation 2)}$$

Thus, for a silicone implantable cardiac lead 14 of diameter 2.08 mm and a conductor 22 diameter of 0.21 mm, the TLZ is approximately 80Ω.

However, this result requires that the conductor 22 be in the center of the implantable cardiac lead 14, similarly to a coaxial cable, and this is not the case in the implantable cardiac lead 14 of FIG. 2. Calculation of TLZ for an implantable cardiac lead having an offset conductor 22 requires formulas of more complexity. A geometrical correction factor x is given by:

$$x = \frac{d^2 + D^2 - 4\delta^2}{2dD} \quad \text{(equation 3)}$$

where δ is the delta or offset of the conductor 22 from the center of the implantable cardiac lead 14 body. The TLZ is then given by:

$$Z_o = 34.6[x + \sqrt{(x^2 - 1)}] \quad \text{(equation 4)}$$

Therefore, since the implantable cardiac lead 14 has a δ of 0.64 mm, the TLZ for the implantable cardiac lead 14 of FIG. 2 would be 62.6Ω, which is less than the TLZ of the centered conductor. The thin layer of ETFE 38 would very slightly increase the TLZ because the permittivity of ETFE is about 2.5, but this effect is negligible and can be ignored. In addition, a small error is introduced because the outer "conductor" of the transmission line is not metal but blood, which is essentially saline at high frequencies. This small error can also be ignored.

As the conductor 22 migrates towards the exterior of the implantable cardiac lead 14 body, but before the conductor 22 externalizes, a maximum offset δ can be determined by the following equation where the thickness, 0.27 mm, of the ETFE 38 is included since at this point, the layer of ETFE 38 will be outside of the implantable cardiac lead 14 body:

$$D/2 - d/2 = 0.906 \text{ mm} \quad \text{(equation 5)}$$

Figure 3:
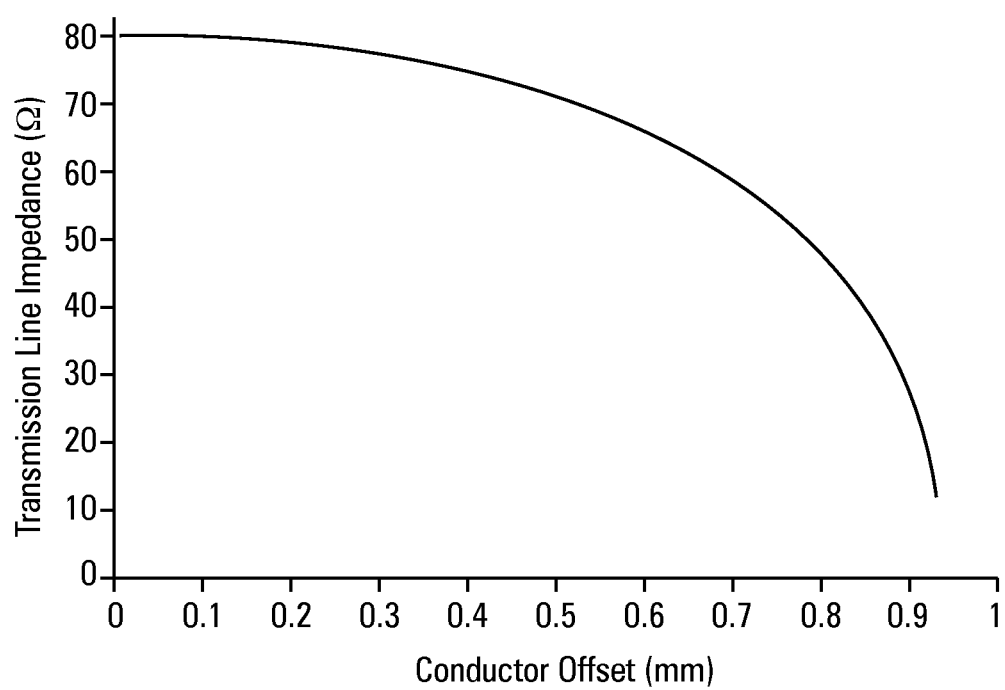
FIG. 3 illustrates the change in transmission line impedance as the conductor migrates towards the outer limits of the implantable cardiac lead body.

And, as is illustrated in FIG. 3, the TLZ drops significantly as the conductor 22 migrates towards the outer limits of the implantable cardiac lead 14 through the silicone body 42.

A fully externalized conductor 22 will provide the ultimate limit of the TLZ:

$$Z_o = 10 \, \Omega = 60 \log_e(D/d)/\sqrt{k} \quad \text{(equation 6)}$$

Where κ=2.5 for ETFE and d=0.27 mm.

Based on these calculations, it is evident that there is a strongly affected physical parameter that would vary with the migration of an internal conductor 22 within a silicone implantable cardiac lead 24 body, even without externalization of the cable or breach of the inner ETFE insulation. It would vary more with externalization of the conductor 22.

In experimentation, a conductor 22 within an implantable cardiac lead 14 was chosen whose migration would be difficult to detect using conventional lead failure techniques. The conductor 22, in this case, is the RV coil with a low frequency impedance of about 60Ω as measured by standard techniques. A saltwater aquarium having a salinity to give a bulk resistivity of 100 Ωcm, thus mimicking the resistivity of blood at high frequencies, was used to contain the implantable cardiac lead 14. A network analyzer was used to measure the real and imaginary impedance for various frequencies.

To begin, the approximate propagation speed V in an implantable cardiac lead, without anomalies, was determined using the following equation:

$$V = c/\sqrt{k} \quad \text{(equation 7)}$$

where c is the speed of light in a vacuum (30 cm/ns). For silicone insulation 42 this results in an approximate propagation velocity of 17.3 cm/ns. This is approximate because the ICD implantable cardiac lead 14 is more complex than a classic coaxial cable having a central conductor.

For an ICD implantable cardiac lead 14 having a common length of 65 cm, the "round-trip" travel distance for wave propagation is 130 cm. The frequency is determined by:

$$f = V/\lambda \quad \text{(equation 8)}$$

where λ is the wavelength of the test frequency. Thus, with a propagation velocity of 17.3 cm/ns, a null at about 130 MHz would be expected as this corresponds to a ½ wavelength over the full length of the implantable cardiac lead 14.

Figure 4:
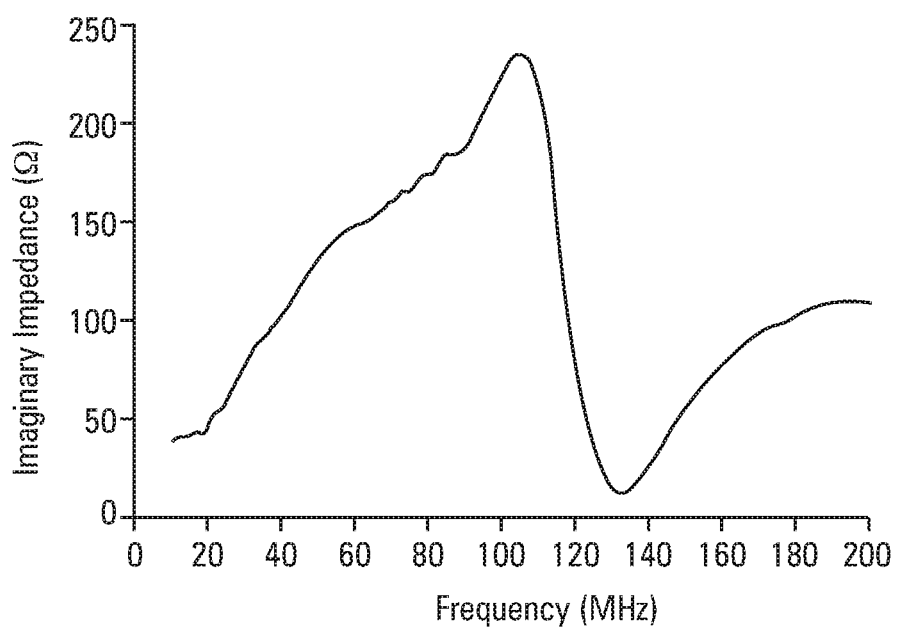
FIG. 4 illustrates the imaginary impedance spectrum for a normal implantable cardiac lead in a saline solution.

Testing was performed on a normal conductor 22, known to be without migration or defects, for frequencies from 10-200 MHz. Each tested frequency was tested two times and the results averaged. As depicted in FIG. 4, detailing an imaginary impedance ($Z_{im}$) spectrum for a normal implantable cardiac lead in saline, a null occurred at 130 MHz thus confirming approximate behavior as a transmission line. Additionally, the peak imaginary impedance ($Z_{im}$) decreased from 235Ω to 200Ω confirming that externalization can be detected with dependence on a critical frequency.

Figure 5:
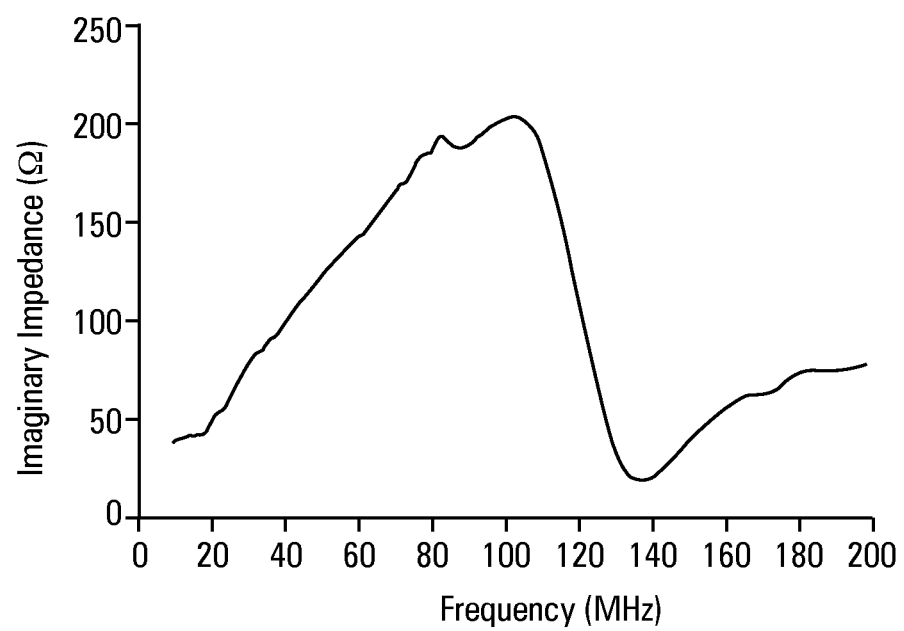
FIG. 5 illustrates the imaginary impedance for an ICD implantable cardiac lead with 1 cm of externalized right ventricular cable.

Testing was then performed on an implantable cardiac lead 14 in which an anomaly was introduced. Due to the difficulty of modeling an internal migration of the conductor 22 within the implantable cardiac lead 14, an ~1 cm defect was introduced near the RV coil, distant from the implantable cardiac lead attachment pins, resulting in a slight externalization of the conductor 22 without conductor 22 exposure (with ETFE 38 intact). The conductor 22 was externalized to ~1 mm from the implantable cardiac lead 14 body. As can be seen in FIG. 5, a spectrum for an implantable cardiac lead 14 with 1 cm of externalized RV conductor 22, the high frequency imaginary impedance ($Z_{im}$) was significantly reduced compared to the implantable cardiac lead 14 without anomalies.

Figure 6:
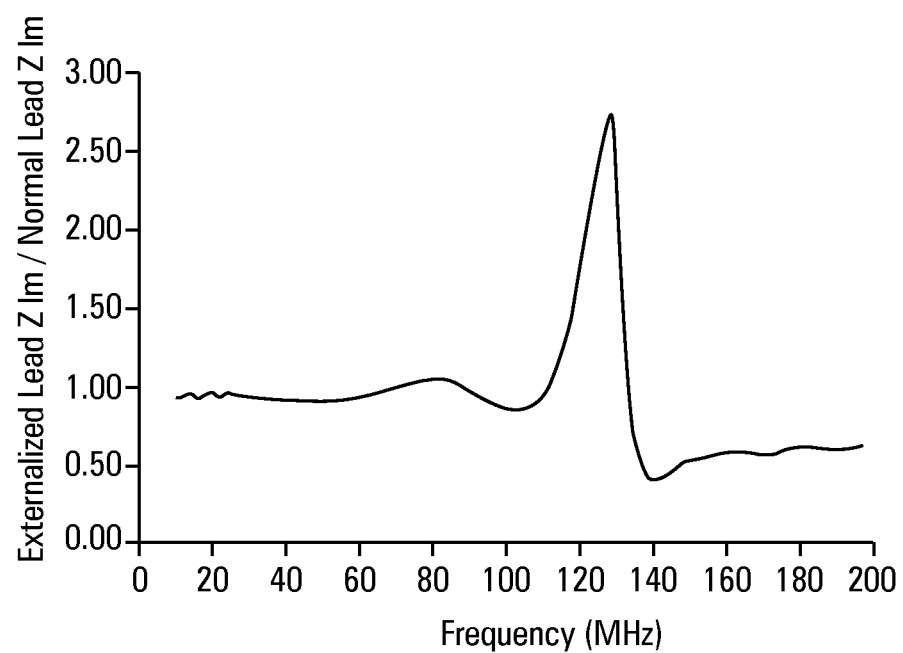
FIG. 6 illustrates the ratio of imaginary impedance for an implantable cardiac lead with externalized cable versus a normal cable.

Ratios of the imaginary impedances were then calculated with the resultant spectrum depicted in FIG. 6. Thus, FIG. 6 depicts the ratio of imaginary impedances for an implantable cardiac lead 14 with an externalized conductor 22 versus an implantable cardiac lead 14 without anomalies. The ratio illustrates a strong peak from about 120 MHz to 133 MHz. And, all of the frequencies about ~140 MHz had a reduced imaginary impedance ($Z_{im}$). Thus, using the testing methods as detailed above, a slight externalization was able to be detected.

As part of the testing process, simple clip conductors were connected to the implantable lead connector pins to give a worse-case test of repeatability since slight variations in implantable cardiac lead connections can influence the transmission line impedance (TLZ).

Further analysis and proofing of the testing method was then performed. For example, for each of the externalized conductor 22 and non-anomaly conductor 22 readings, the difference was calculated at each frequency giving stability values of:

$$S(f) = \text{abs}(Z_{im1} - Z_{im2}) \quad \text{(equation 9)}$$

Figure 7:
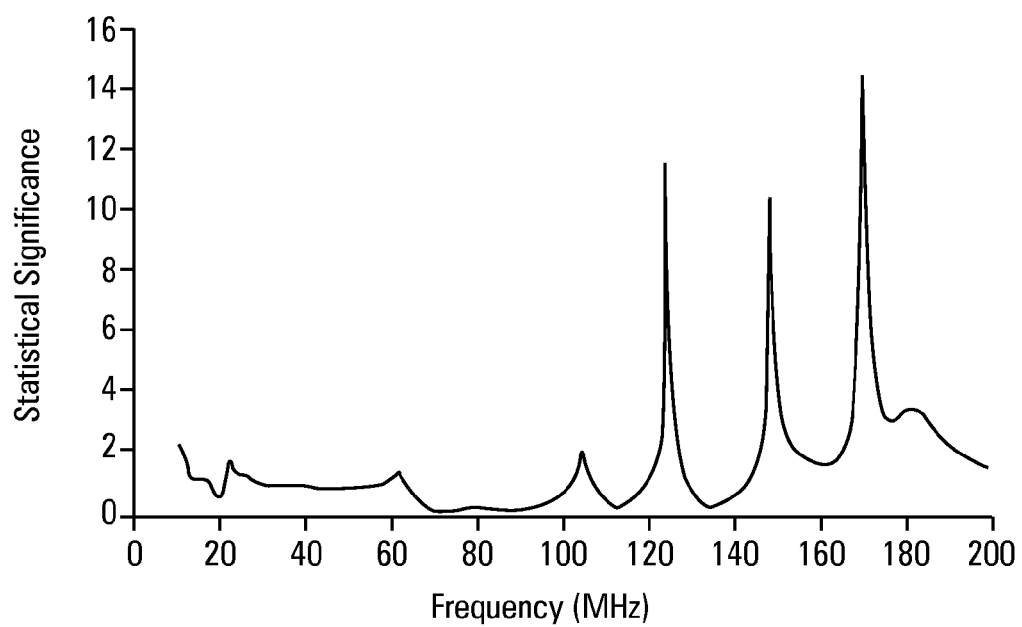
FIG. 7 illustrates the statistical confidence of discrimination.
Figure 8:
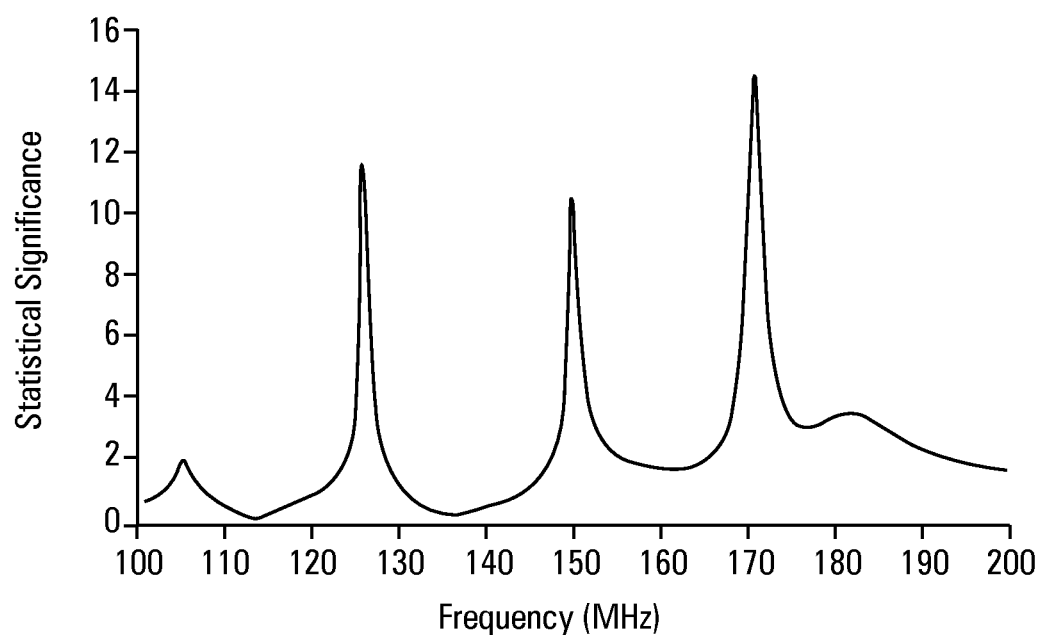
FIG. 8 illustrates the statistical confidence of discrimination for 100-200 MHz.

The statistical confidence was then calculated using the formula:

$$\text{Confidence} = \frac{\text{abs}(Z_{im}\ \text{normal} - Z_{im}\ \text{externalized})}{S\text{normal} + S\text{externalized}} \quad \text{(equation 10)}$$

resulting in FIG. 7, a statistical confidence of discrimination. A 19-point moving average of the confidence values was used to reduce spurious values and arrive at the statistical significance. As can be seen in FIG. 7, there is a minimal statistical confidence in the reading differences below 100 MHz so these are not shown in FIG. 8 (a statistical confidence of discrimination for 100-200 MHz). As illustrated, a value greater than 2 shows high confidence in the discrimination power. The technique as described has high statistical significance for frequencies of 123-127 MHz, 147-154 MHz, and 166-189 MHz.

A valued clinical measurement has both "clinical" significance (i.e. the value changes greatly) but also "statistical" significance (i.e. the changes are not due to noise). Thus, a "utility" value can be calculated at each frequency with the formula given as:

Utility=% change×statistical confidence  (equation 11)

Figure 9:
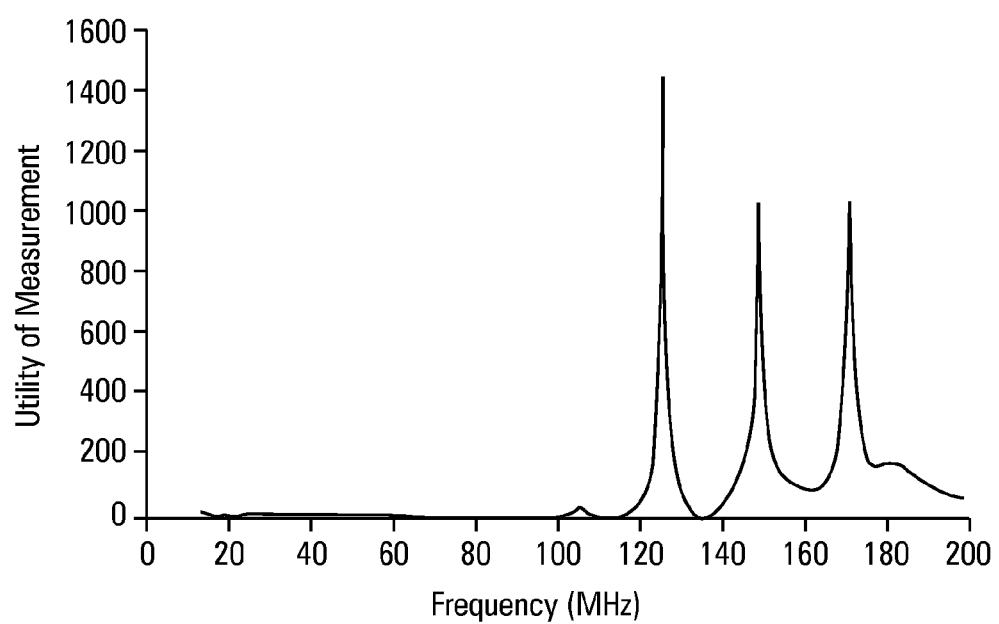
FIG. 9 illustrates the spectrum of utility of measurement.
Figure 10:
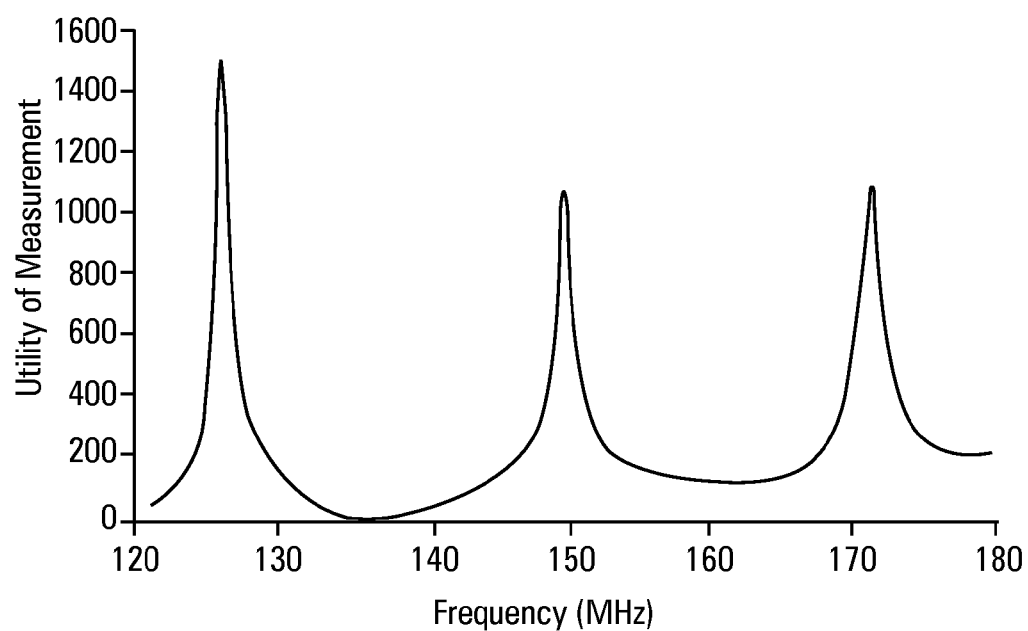
FIG. 10 illustrates the utility of measurement for 120-180 MHz.

A "utility" value of 200 corresponds to a 100% change with a statistical confidence of 2.0. This combination is unusually strong for any type of clinical diagnosis. The utility values are depicted in FIGS. 9 and 10, with FIG. 10 showing the utility of measurement for the 120 MHz to 180 MHz spectrum only. In this embodiment, the present invention has recognized that a shift in the imaginary impedance at the frequencies 123-128 MHz, 146-153 MHz and 168-176 MHz gives a powerful diagnostic of a conductor 22 externalization. The peak at 125 MHz corresponds to the implantable cardiac lead length and the externalization was introduced at 50 cm from the beginning of the implantable cardiac lead 14 (connection pins). For the 50 cm distance to the externalization, the full-wavelength critical frequency is given by:

$$f = V/\lambda \quad \text{(equation 12)}$$

where λ is the wavelength of the test frequency. Thus, with a propagation velocity of 17.3 cm/ns, a null at about 172 MHz would be expected as this corresponds to a one-quarter wavelength over this distance. And, while there is no simple explanation for the middle peak at 150 MHz, it is clearly demonstrated as a result of the experimentation.

Figure 11:
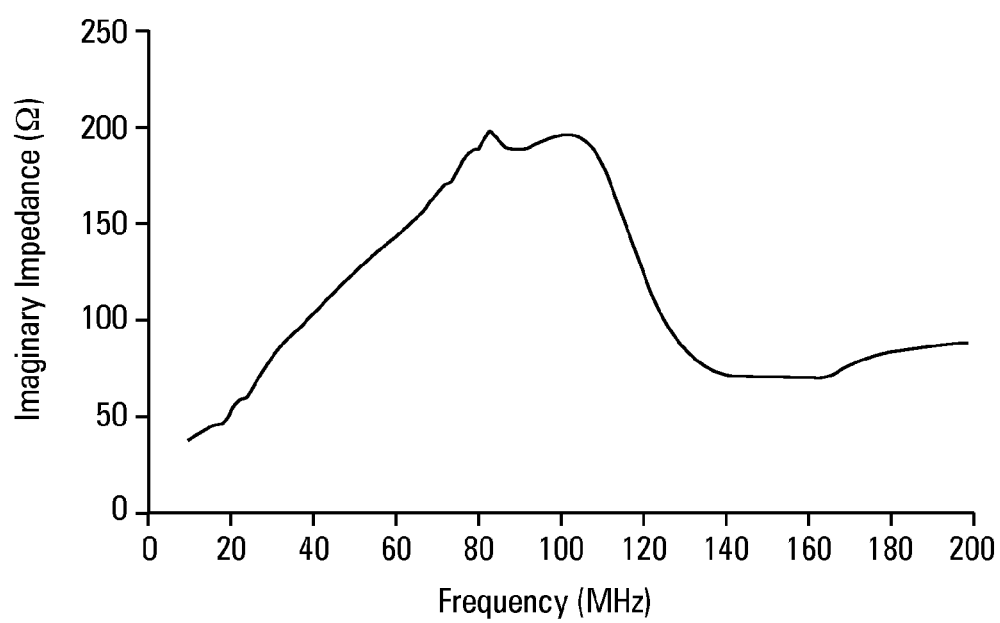
FIG. 11 illustrates the imaginary impedance with an exposed conductor.

Further experimentation was performed using the imaginary impedance component to detect conductor 22 exposure (ETFE 38 not intact). The conductor 22 was exposed by removing approximately 2-3 mm of ETFE 38 insulation. Testing was performed, similarly as detailed above for a conductor with no anomalies and an externalized conductor, and FIG. 11 depicts that the imaginary impedance at high frequencies was able to detect conductor exposure.

Figure 12:
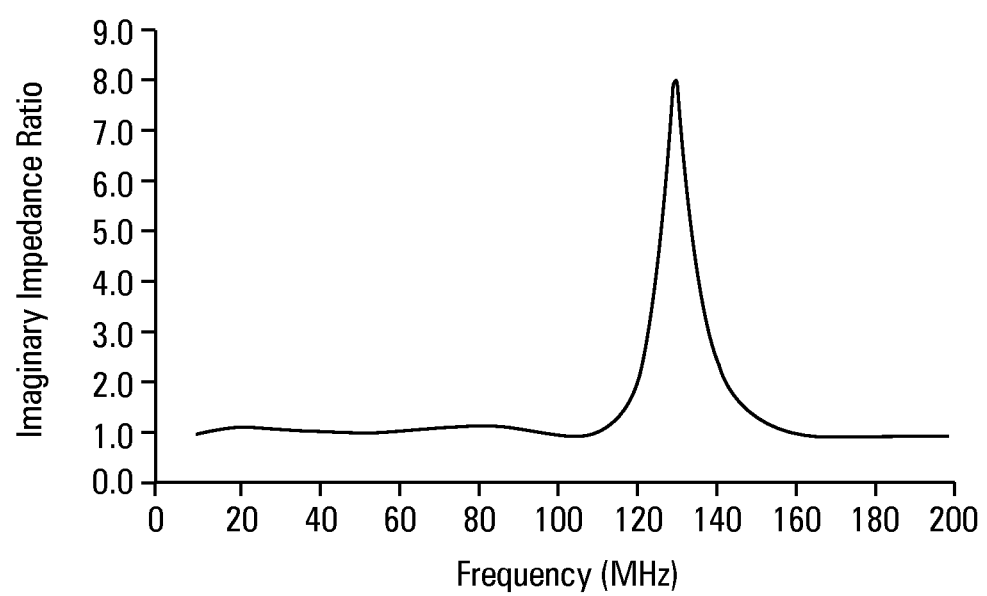
FIG. 12 illustrates the ration of imaginary impedance for an implantable cardiac lead with an exposed conductor in a normal cable.
Figure 13:
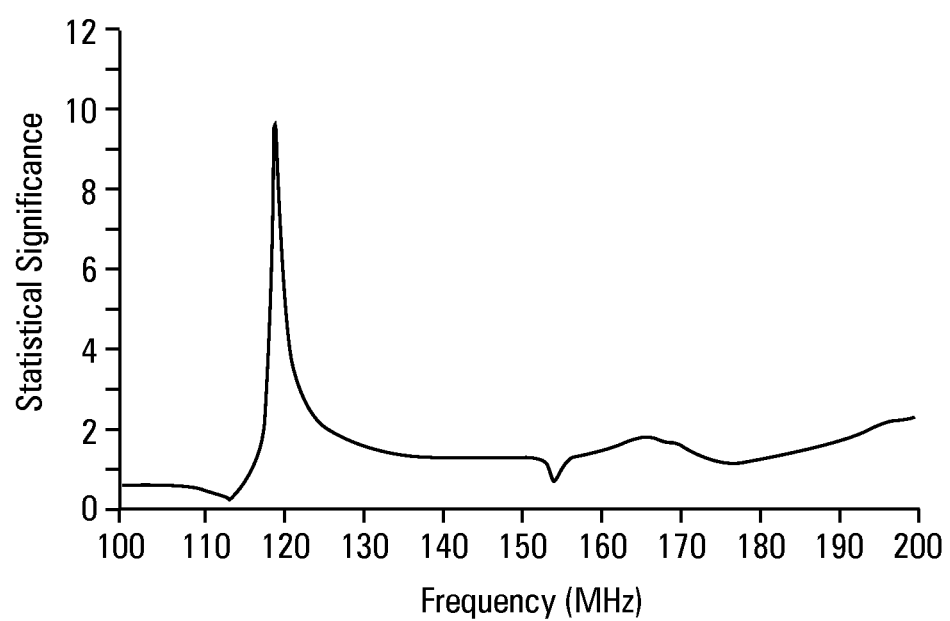
FIG. 13 illustrates the statistical confidence of discrimination.

As can be seen in FIGS. 12 and 13, the changes in imaginary impedance are even greater for an exposed conductor than for one that is externalized. FIG. 12 illustrates the ratio of $Z_{im}$ for an implantable cardiac lead with exposed conductors and the impedance increase has a pronounced peak at 131 MHz. FIG. 13 depicts the statistical confidence of discrimination with a peak at 120 MHz.

Figure 14:
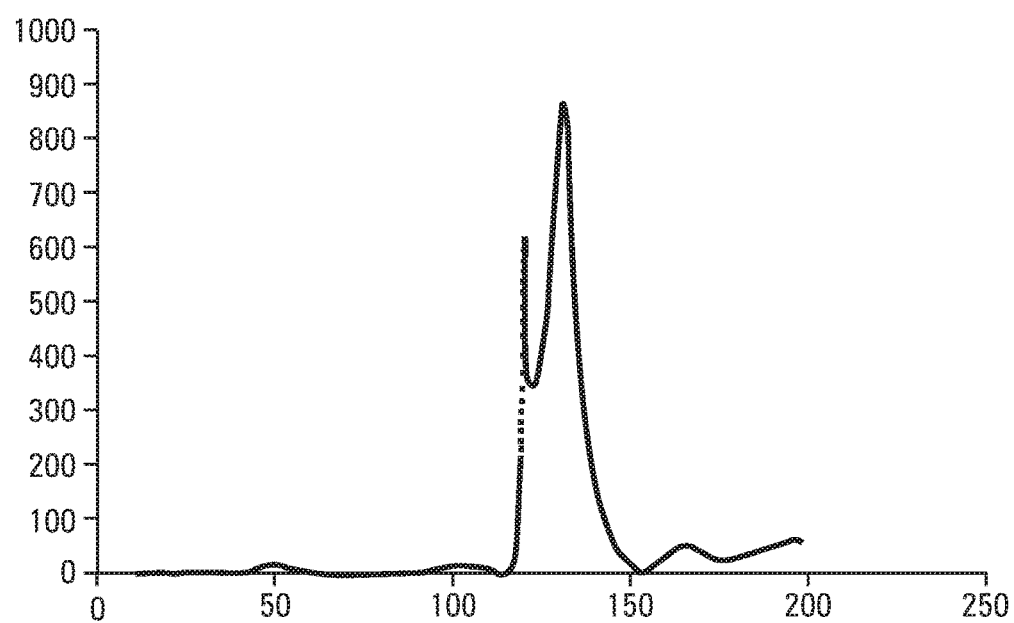
FIG. 14 illustrates the spectrum of measurement utility for an imaginary impedance ration for an exposed conductor.

FIG. 14 further depicts the spectrum of measurement utility for an imaginary impedance ratio for the exposed conductor 22. This illustrates strong diagnostic capability of this method from 119-139 MHz with a peak at 130 MHz.

Figure 15:
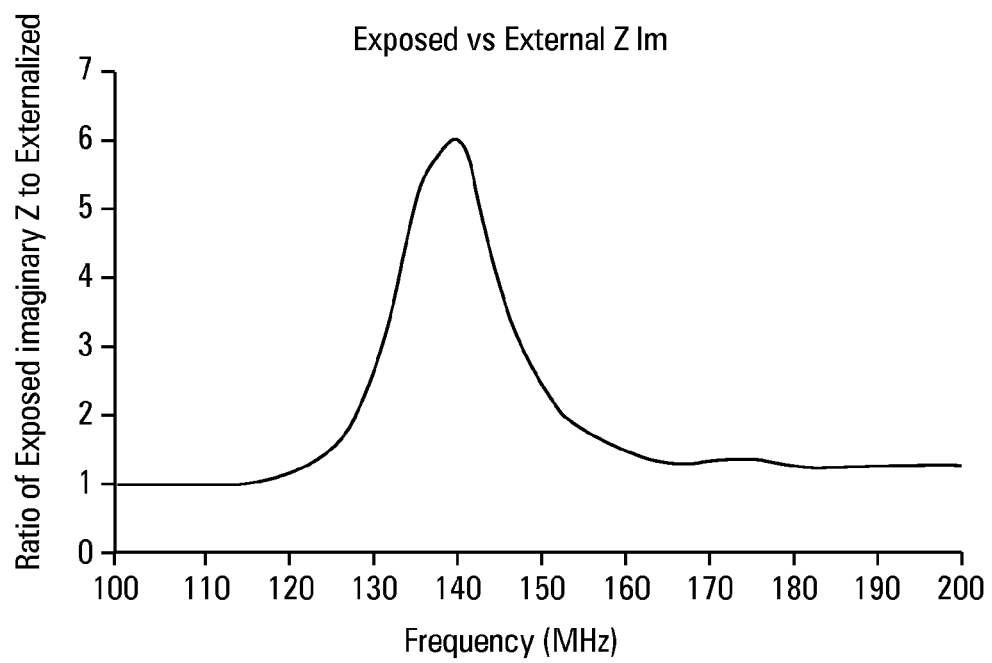
FIG. 15 illustrates the ratio of imaginary impedance for an implantable cardiac lead with an exposed conductor versus an externalized cable.

In another embodiment, the imaginary impedance component can be used to differentially detect conductor exposure versus conductor externalization. An advantage to determining the type of anomaly is that a determination can be made as to the urgency of replacing the implantable cardiac lead 14. FIG. 15 depicts the ratio of $Z_{im}$ for an implantable cardiac lead with an exposed conductor versus an externalized conductor.

Figure 16:
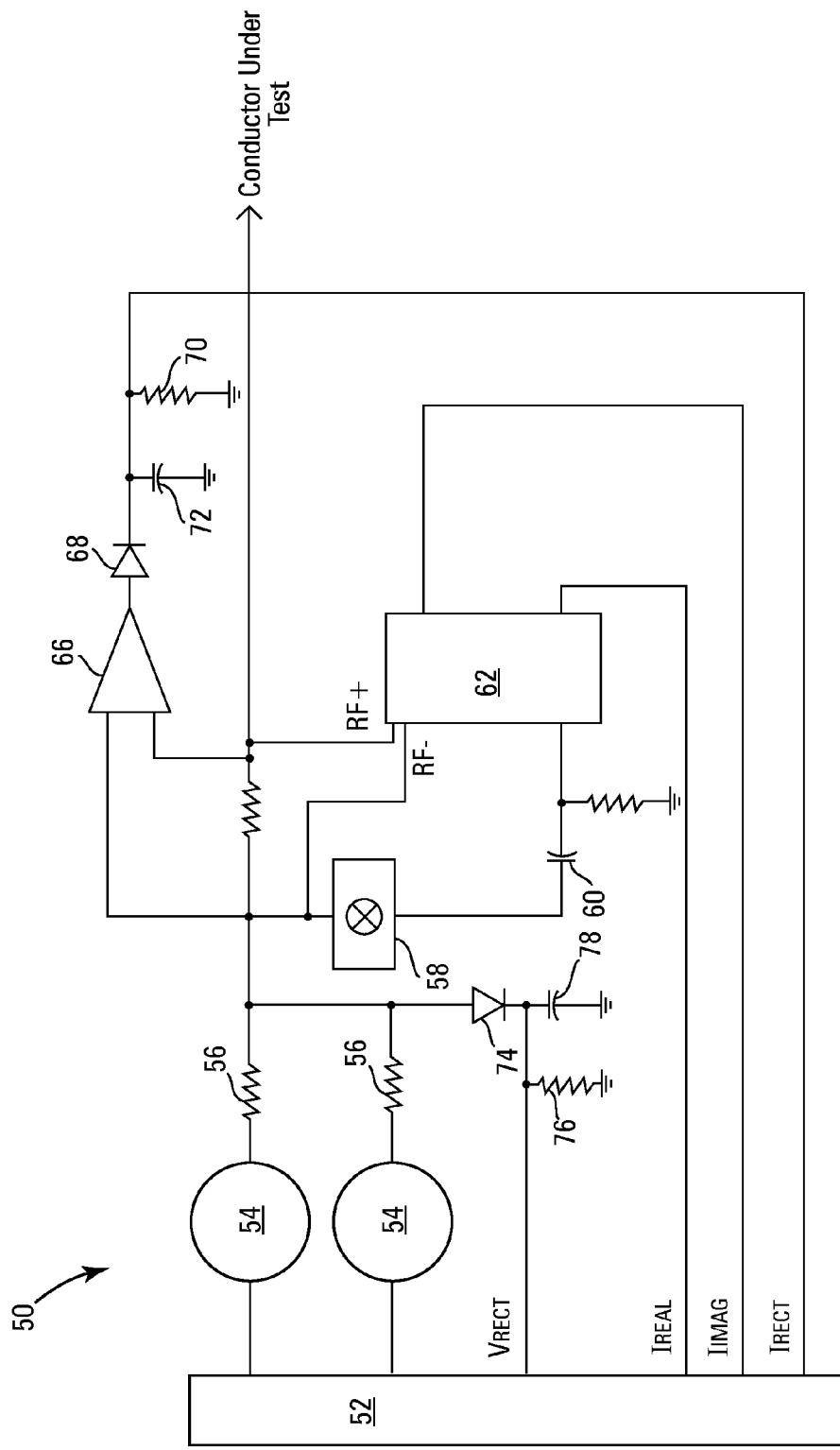
FIG. 16 illustrates an embodiment of stand-alone implantable lead tester circuitry for high-frequency implantable lead testing.

The examples in the above methods assume that the test signals would be generated from within the implantable pulse generator via special testing apparatus 50, as depicted in FIG. 16, stand-alone lead tester circuitry 50 for high-frequency lead testing. Microcontroller (μC) with analog I/O 52 controls the system 50. Microcontroller (μC) 52 sweeps thru frequencies of interest by delivering appropriate voltages to at least 1 voltage-controlled oscillator (VCO) 54. As an example, the VCO 54 could be the Crystek CVCO33CL-0110-0150 which sweeps the range 130-150 MHz thus capturing the $1^{st}$ peak as shown in FIG. 7. A plurality of VCOs 54 can be configured to capture additional peaks and the outputs can be summed via resistors 56.

This outputted signal:

$$V(t) = \sin(2\pi ft) \quad \text{(equation 13)}$$

is then fed to the input of the high-frequency (500 MHz) multiplier 58, an example being the Analog Devices AD834. The multiplier provides a squaring function resulting in an output voltage of:

$$\sin^2(2\pi ft) = \tfrac{1}{2} - \tfrac{1}{2}\cos(4\pi ft) \quad \text{(equation 14)}$$

which is fed through DC blocking capacitor converting the signal to:

$$\tfrac{1}{2}\sin(4\pi ft) \quad \text{(equation 15)}$$

by removing the ½ offset and phase shifting the −cos into a sin function. Note that the frequency is now doubled. The doubled frequency signal is fed into a Quadrature Demodulator 62 as the "carrier" signal. An example of a Quadrature Demodulator 62 is the Linear Technology LT5517 which can perform up to 900 MHz.

The sense resistor $R_s$ senses the current (as a voltage drop). The voltage drop is fed to the Quadrature Demodulator 62 as the RF signal. An impedance matching LC network is provided prior to the RF inputs of the Quadrature Demodulator 62 but the details are omitted in the figure for clarity. The Quadrature Demodulator 62 outputs the real and imaginary components of the current ($I_{REAL}$ and $I_{IM}$ respectively) which are then fed to the μC 52.

The sensed current signal is amplifier 66 isolated, rectified and smoothed with the diode 68, resistor 70 and capacitor 72. The DC signal is then fed back to the μC 52 as $I_{RECT}$. The VCO voltage is also rectified and smoothed with the diode 74, resistor 76, and capacitor 78. The DC signal is then fed back to the μC 52 as $V_{RECT}$.

The vector value of the impedance is calculated by the μC 52 as:

$$Z_{abs} = V_{RECT}/I_{RECT} \quad \text{(equation 16)}$$

The µC 52 further calculates the real and imaginary components of the impedance from $I_{REAL}$ and $I_{IM}$.

Figure 17:
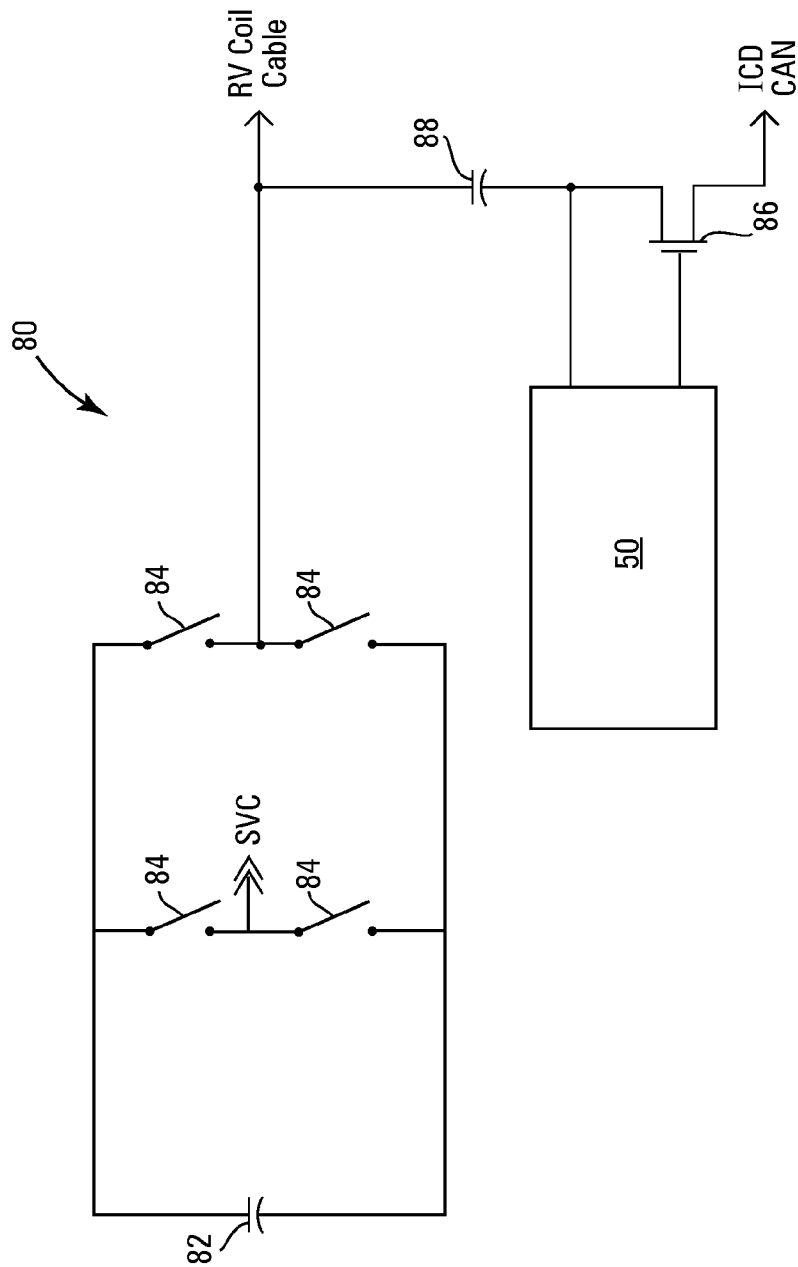
FIG. 17 illustrates an embodiment of an implantable lead tester disposed within an ICD.

FIG. 17 is an embodiment of an implantable lead tester 50 housed within an ICD 80. An energy storage capacitor 82 provides energy to the H-bridge shown with the 4 switches 84. The output of the H-bridge drives the RV coil cable. In conventional ICDs, this signal passes thru a feed-thru capacitor having a typical value of 1 nF designed to block RF interference, for example, a mobile phone in a shirt pocket. Unfortunately, at the frequencies of interest, the feed-thru capacitor represents a shunt of about 1Ω to ground thus precluding impedance spectrum measurements:

$$Z = 1/(2\pi f) = 1.13\Omega \text{ at } 140 \text{ MHz} \quad \text{(equation 17)}$$

In order to perform implantable lead testing as disclosed and to prevent the shunting operation, an embodiment of the implantable lead tester uses a high voltage MOSFET 86 to connect the 1 nF capacitor 88 to the ICD can. The impedance measuring circuit 50 is provided in parallel to the output of the capacitor 88 and the gate of the MOSFET 86. During impedance spectral testing, MOSFET 86 is open and the impedance testing signal is fed thru the impedance measuring circuit 50 (a standard MOSFET control circuit is not shown for clarity). During normal operation the MOSFET is ON, the signal bypasses the impedance measuring circuit 50, and the capacitor 88 serves to shunt interference. In addition, the MOSFET 86 protects the impedance measuring circuitry 50 from defibrillation shocks. Similar circuitry is used for the lower-voltage pacing and sensing connections.

In an alternative embodiment, the impedance spectral testing signal is fed thru the non-capacitive feed-thru that is used by the RF communications antenna. A magnetic reed switch or MOSFET is then used to connect this "antenna" signal to the appropriate cable in the ICD lead.

Testing Results

Figure 18:
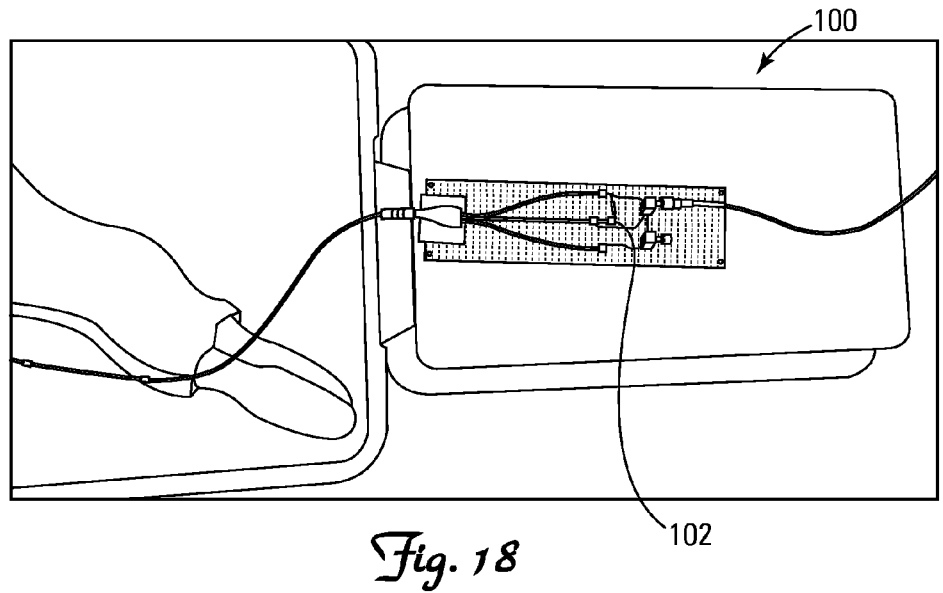
FIG. 18 depicts the connection jig to give repeatable impedance connections as used in testing conductors.

As discussed above, in experimentation, conductors 22 within an implantable cardiac lead 14 were chosen whose migration would be difficult to detect. One conductor 22 is the RV coil with a low frequency impedance of about 60Ω as measured by standard techniques. The second conductor 22 is the ring conductor. A saltwater aquarium 100 having a salinity to give a bulk resistivity of 100 Ωcm, thus mimicking the resistivity of blood at high frequencies, was used to contain the implantable cardiac lead 14. As shown in FIG. 18, a custom built connection jig 102 was used to give repeatable impedance connections. A network analyzer was used to measure the real and imaginary impedance for various frequencies.

Figure 19:
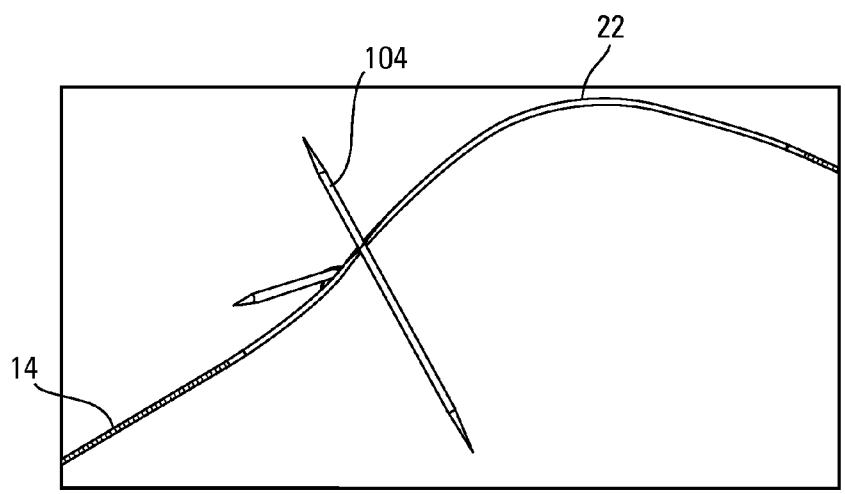
FIG. 19 depicts the method of externalizing the conductor with the use of a toothpick for testing.

Testing was performed on externalized RV coil conductors 22, externalized ring conductors 22, and exposed RV coil conductors 22. Tested were five Riata® 65.0 cm leads 14 for each of the test scenarios. For each lead 14, the conductors 22 were either externalized or exposed at 9.0 cm from tip (n=2) and 18 cm from tip (n=3). Externalization was to the precise thickness of a standard wooden toothpick 104 as shown in FIG. 19. For externalization of the RV coil conductors 22 and the externalized ring conductors 22, the real and imaginary impedance was tested from 10 MHz to 1000 MHz with the lead in saline at 100 Ω cm resistivity.

First, the RV coil conductors 22 were externalized. FIG. 20 is a table that details the lead name, lead serial number, model number, and the distance from tip where the externalization was introduced.

The beginning for the RV coil is 58.5 cm from the lead 14 connection. Assuming a dielectric constant of 3.0 for the silicone this would give a half-wave frequency of ~150 MHz. Indeed, the $Z_{real}$ peaked at approximately 500Ω while $Z_{Imag}$ was about 0 at 150 MHz thus confirming reasonable transmission line behavior. The $Z_{mean}$ shift was calculated for all five leads 14. Also, the number of standard deviations (NSD) of shift was calculated for each lead 14 at each frequency. The standard deviation was determined from the five leads 14 before modifications.

Figure 21:
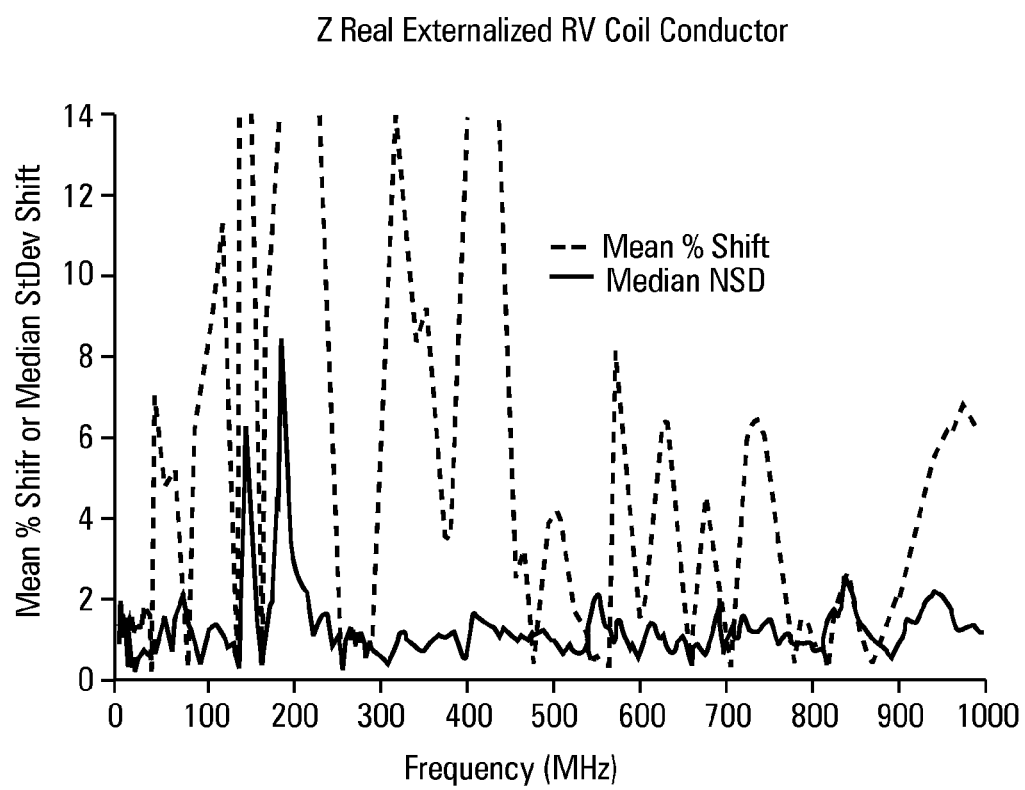
FIG. 21 illustrates the test results of changes in $Z_{real}$ with externalization on the RV coil conductor.
Figure 22:
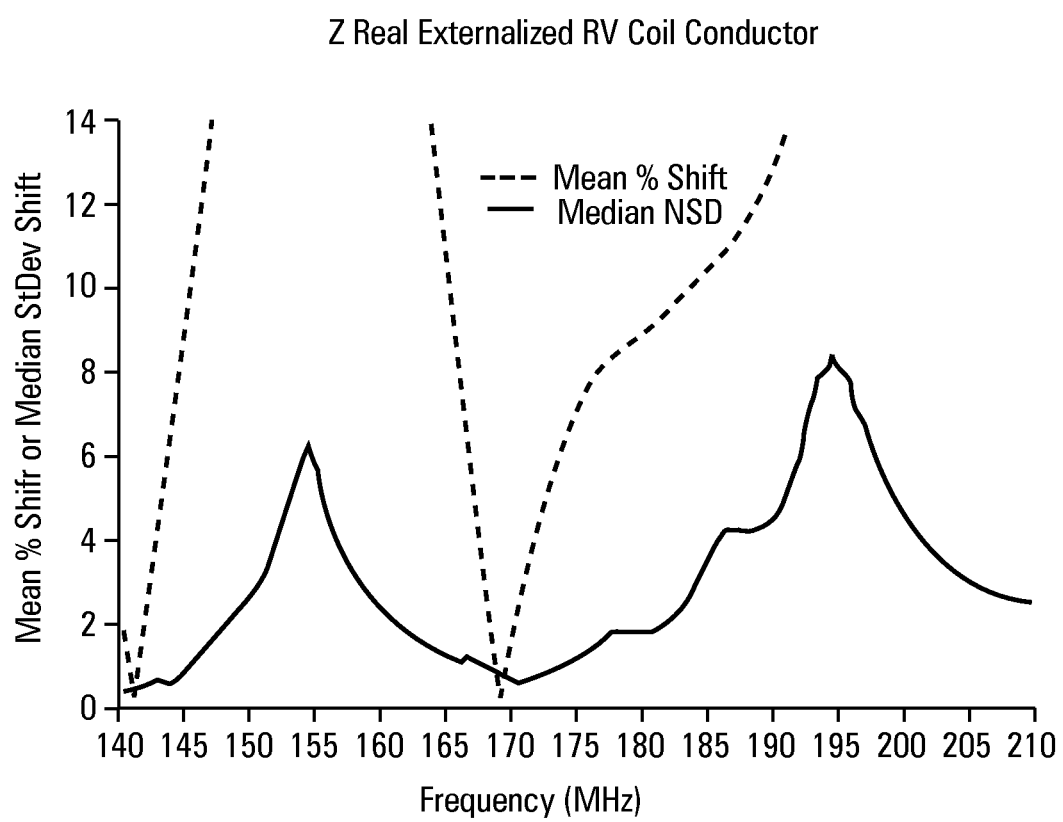
FIG. 22 illustrates the test results of changes in $Z_{real}$ with externalization from 140 MHz to 210 MHz on the RV coil conductor.

As seen in FIG. 21, there were two strong peaks with 6- and 8-sigma shifts. These shifts each had percent shifts of >>10% which was the threshold set for accuracy confidence. As seen in FIG. 22, these peaks are quite robust. The peak at 195 MHz has a confidence of >4 sigma from approximately 186 MHz to approximately 204 MHz.

Figure 23:
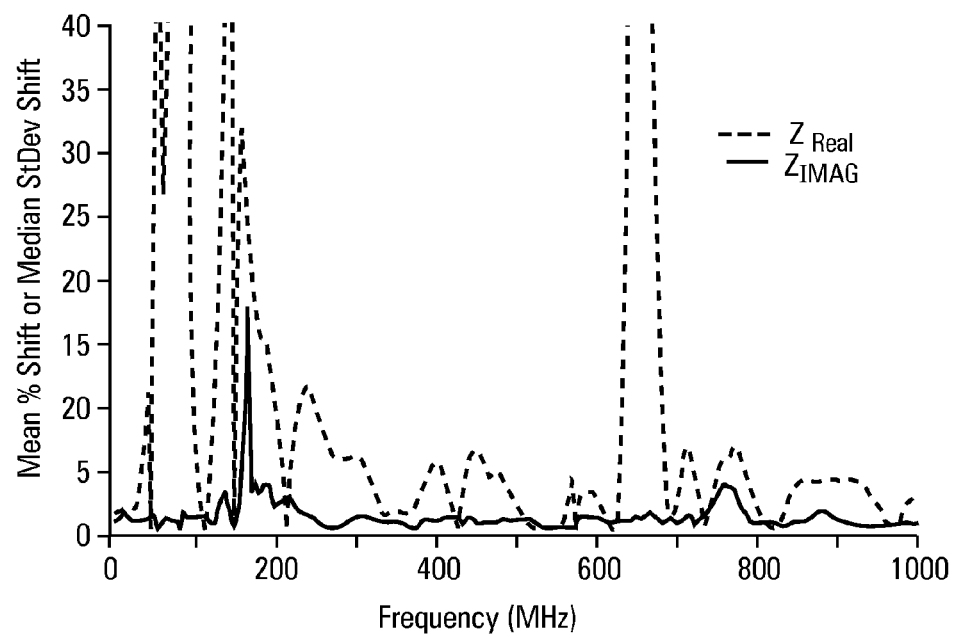
FIG. 23 illustrates the test results of changes in $Z_{imag}$ with externalization on the RV coil conductor.
Figure 24:
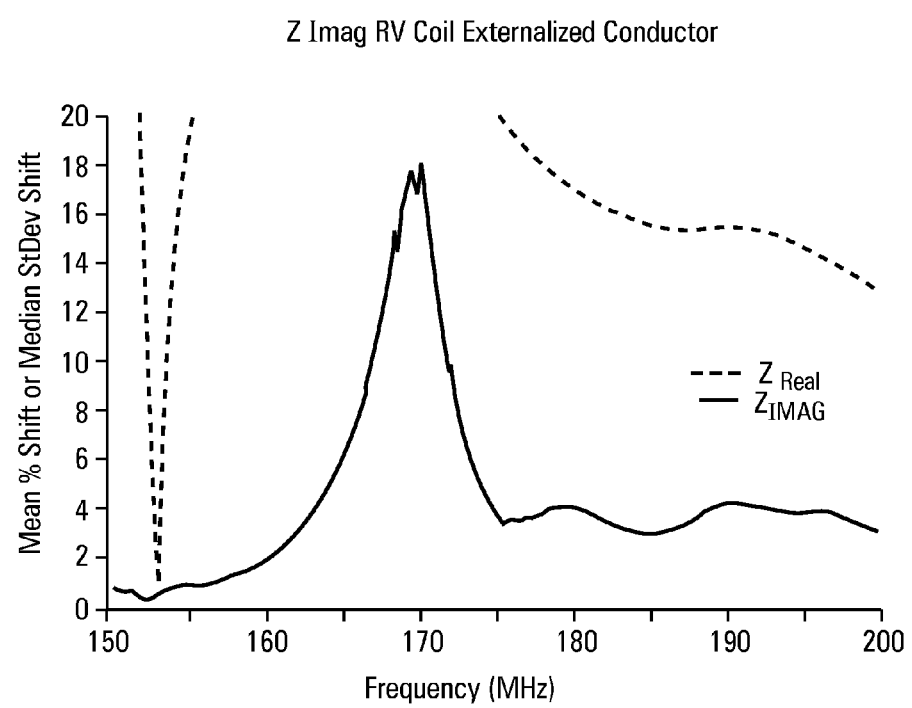
FIG. 24 illustrates the test results of changes in $Z_{imag}$ with externalization from 150 MHz to 200 MHz on the RV coil conductor.
Figure 25:
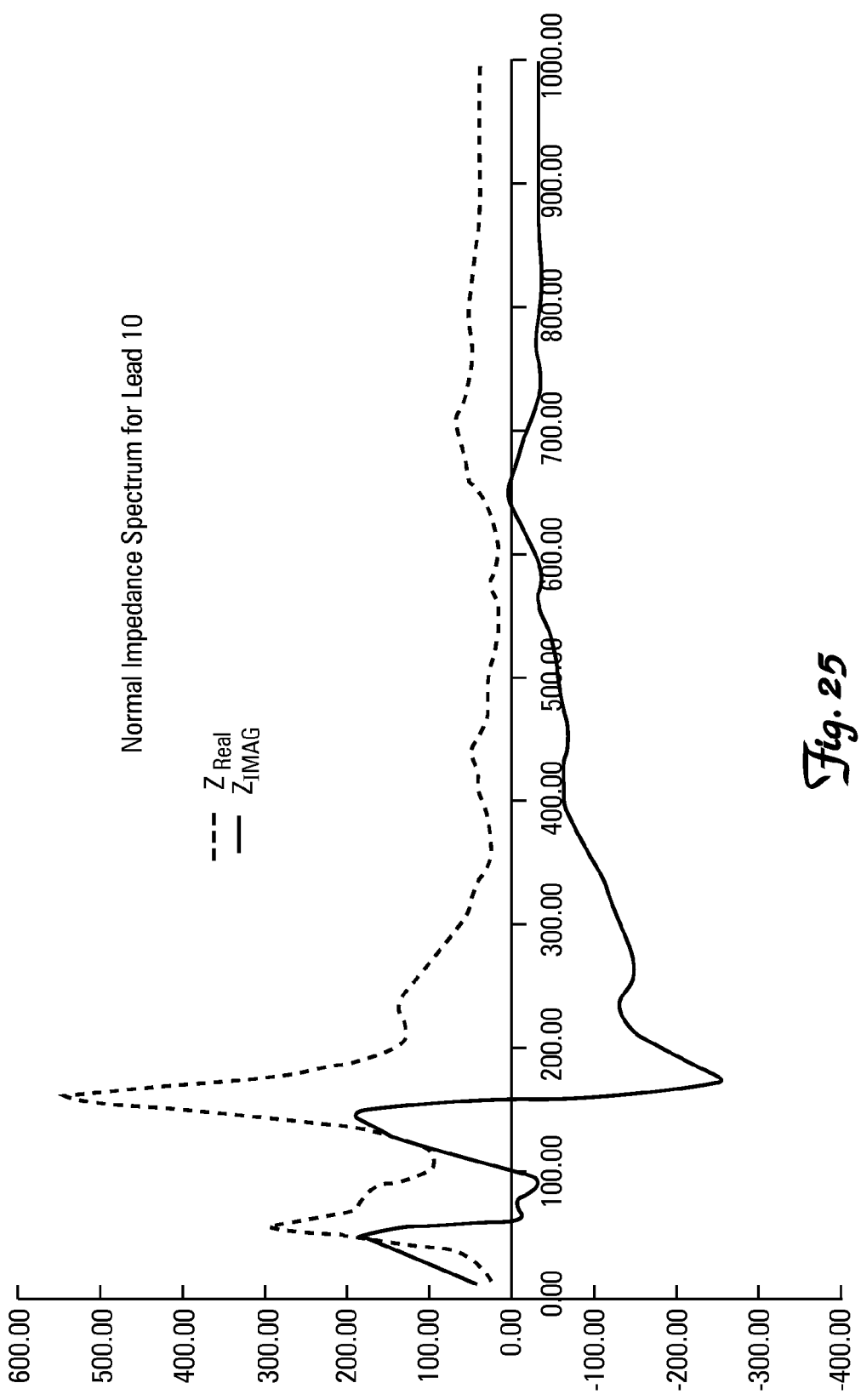
FIG. 25 illustrates lead 10 in normal condition during testing on the RV coil conductor.
Figure 26:
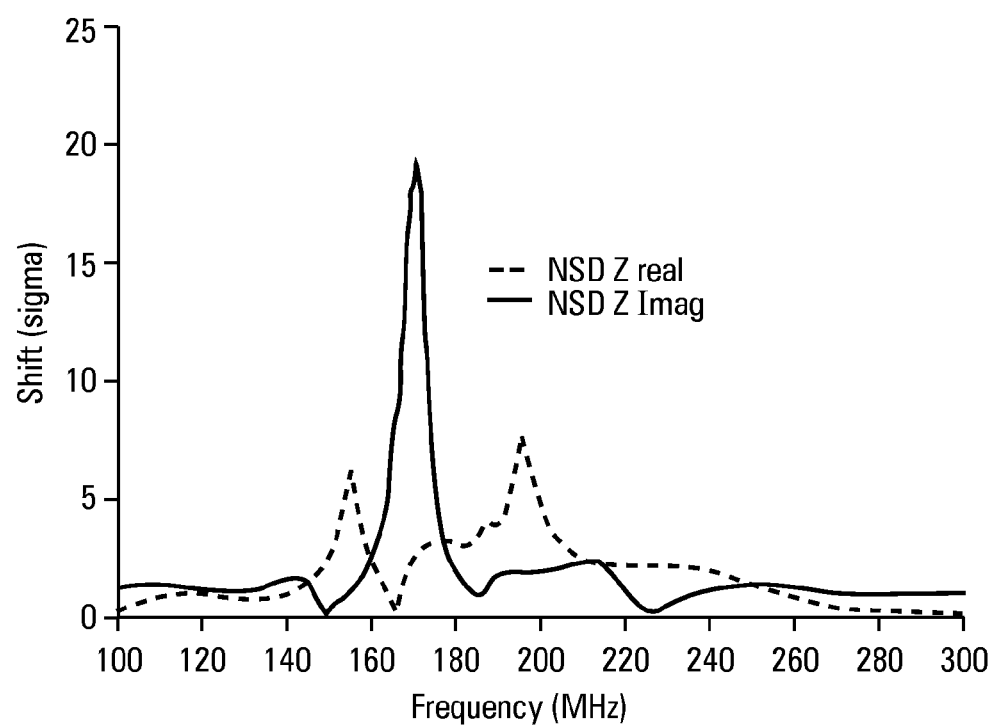
FIG. 26 illustrates lead 10 after externalization of the RV coil conductor during testing.
Figure 27:
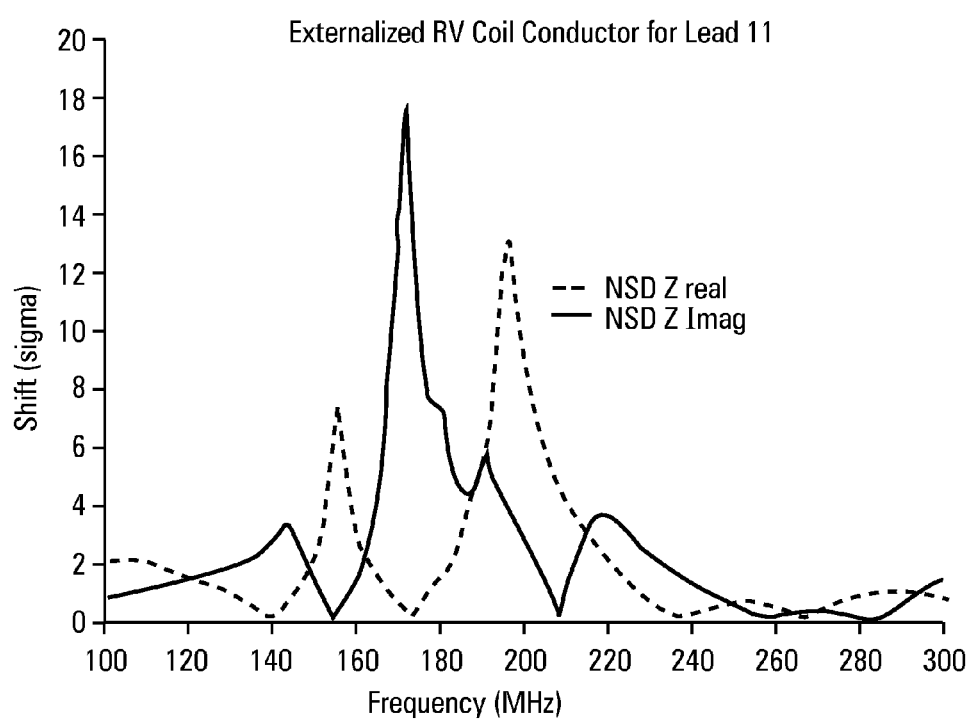
FIG. 27 illustrates lead 11 after externalization of the RV coil conductor during testing.
Figure 28:
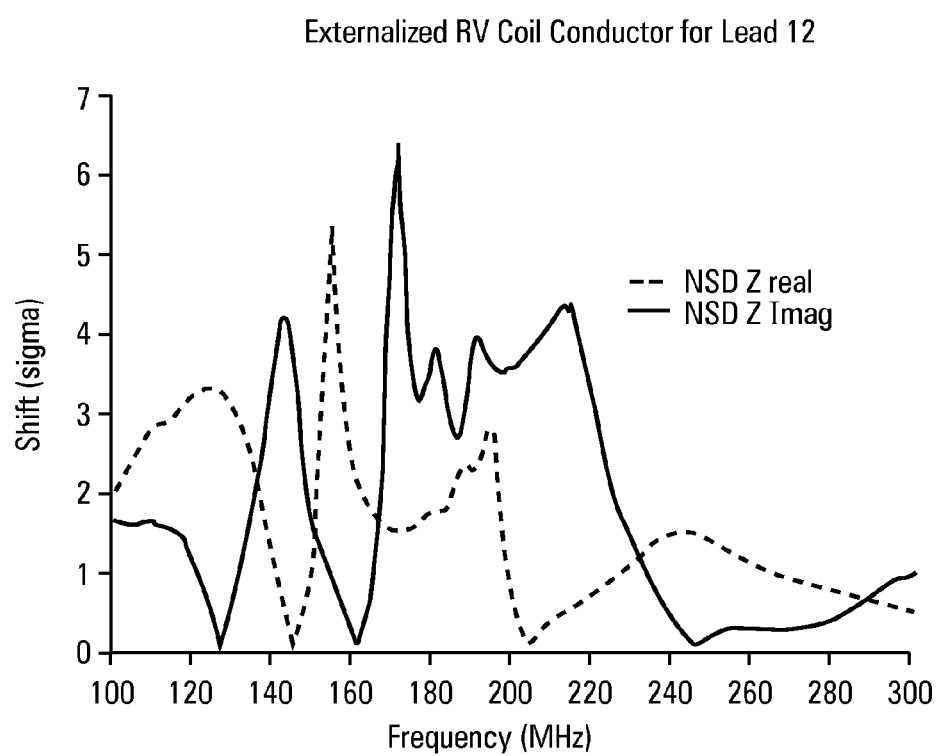
FIG. 28 illustrates lead 12 after externalization of the RV coil conductor during testing.
Figure 29:
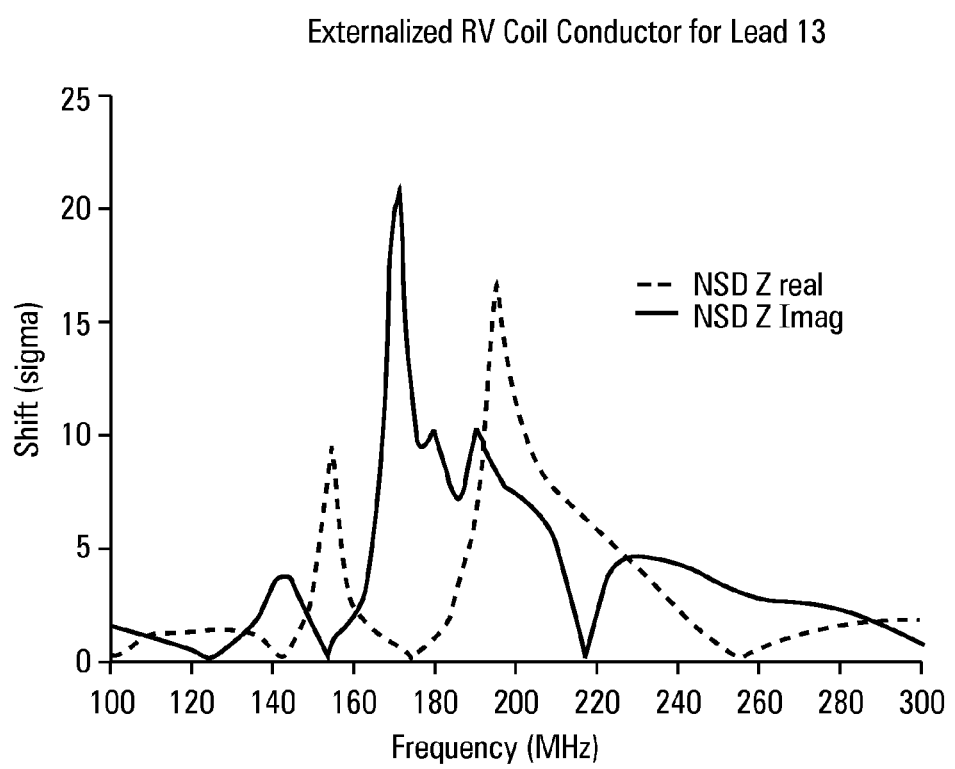
FIG. 29 illustrates lead 13 after externalization of the RV coil conductor during testing.
Figure 30:
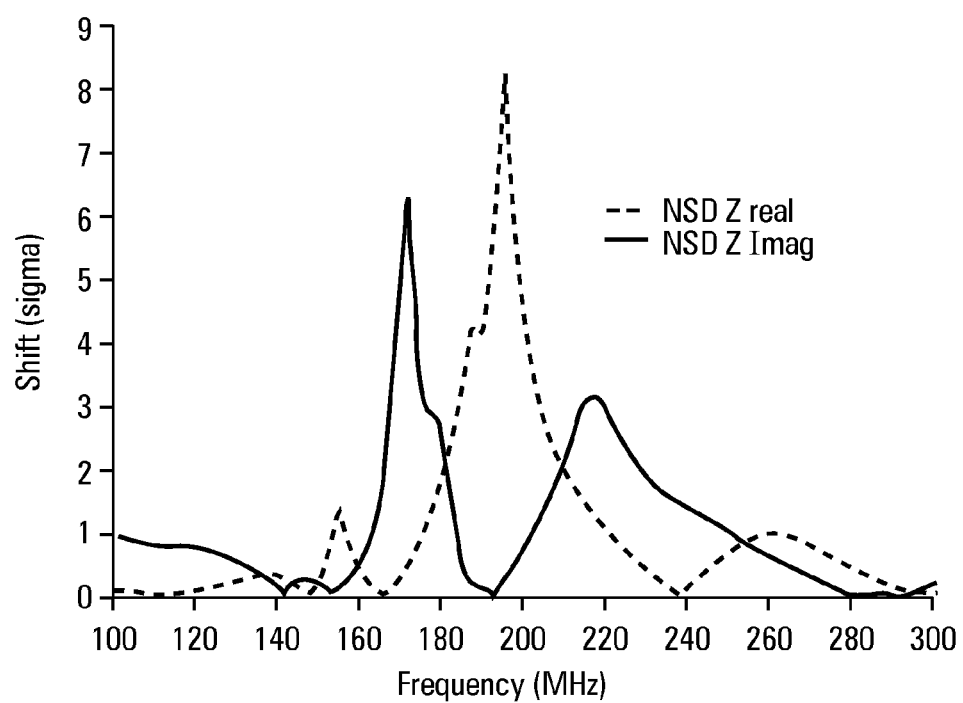
FIG. 30 illustrates lead 14 after externalization of the RV coil conductor during testing.

As seen in FIG. 23, there is a single strong peak in the $Z_{imag}$ response. This single strong peak is seen zoomed in FIG. 24 and has a peak of 18 sigma at approximately 170 MHz. It has statistical confidence of >4 sigma from 164 MHz to 175 MHz. Shown in FIG. 25 is a normal impedance spectrum for Lead 10. This normal impedance spectrum is similar to the normal impedance spectrum for Leads 11 to 14. The spectral shifts in FIG. 25 are shown for about 100 MHz to about 250 MHz as these have the frequencies where the shifts are statistically significant. FIGS. 26 to 30 are individual lead impedance spectral shifts with externalization for Leads 10 to 14. With the conductor externalized there is an increase in $Z_{imag}$ at about 170 MHz and a drop in $Z_{real}$ at about 195 MHz.

Thus, based on testing results, it can be concluded that externalization can be detected with a high degree of confidence by noting changes in the $Z_{real}$ at 195 MHz and $Z_{imag}$ at 170 MHz. It is understood that the range of 170 MHz to 195 MHz is but one possible embodiment. In general, the embodiments may encompass the ranges of 150 MHz to 250 MHz. Other embodiments could also encompass the ranges of 170 MHz to 200 MHz. And, yet, other embodiments could also encompass the ranges of 190 MHz to 220 MHz. It is further understood that frequencies used in these embodiments may differ based on the type, length or configuration of leads or plugs used. Thus, critical frequencies can be different for various lead types.

Second, testing was performed for the detection of an exposed RV coil conductor 22. An ETFE ribbon having a length of approximately 5 mm was scraped off the conductor 22 at the site of the externalization and the impedance spectrum measurements were repeated.

Figure 31:
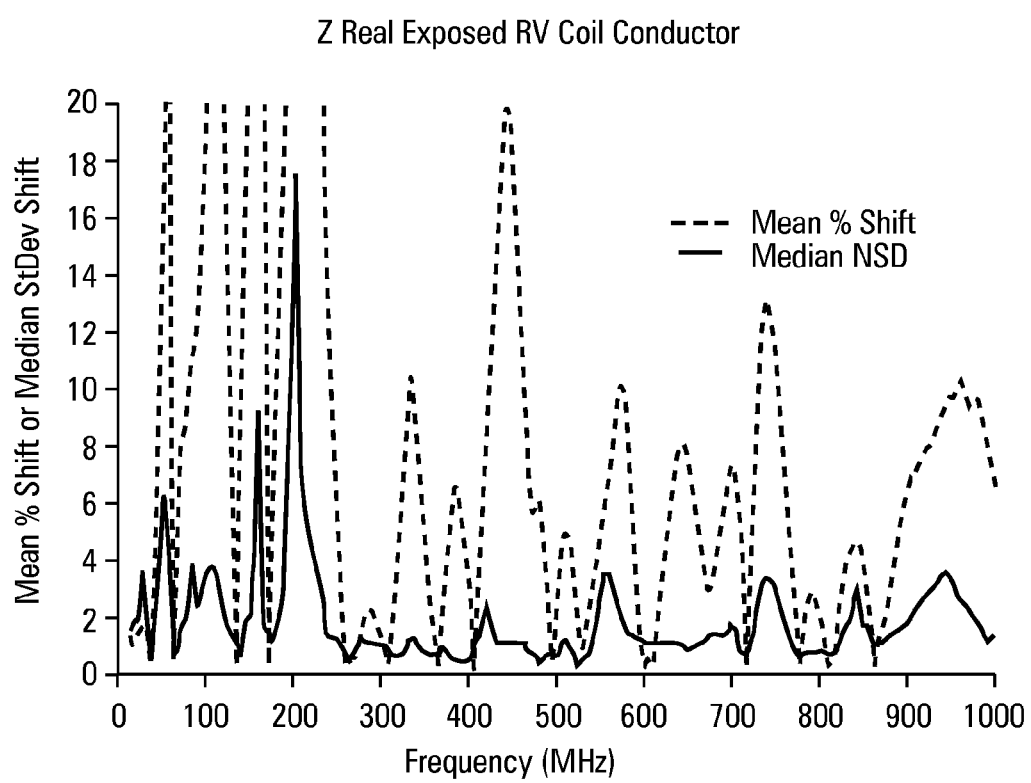
FIG. 31 illustrates the test results of changes in $Z_{real}$ with exposure on the RV coil conductor.
Figure 32:
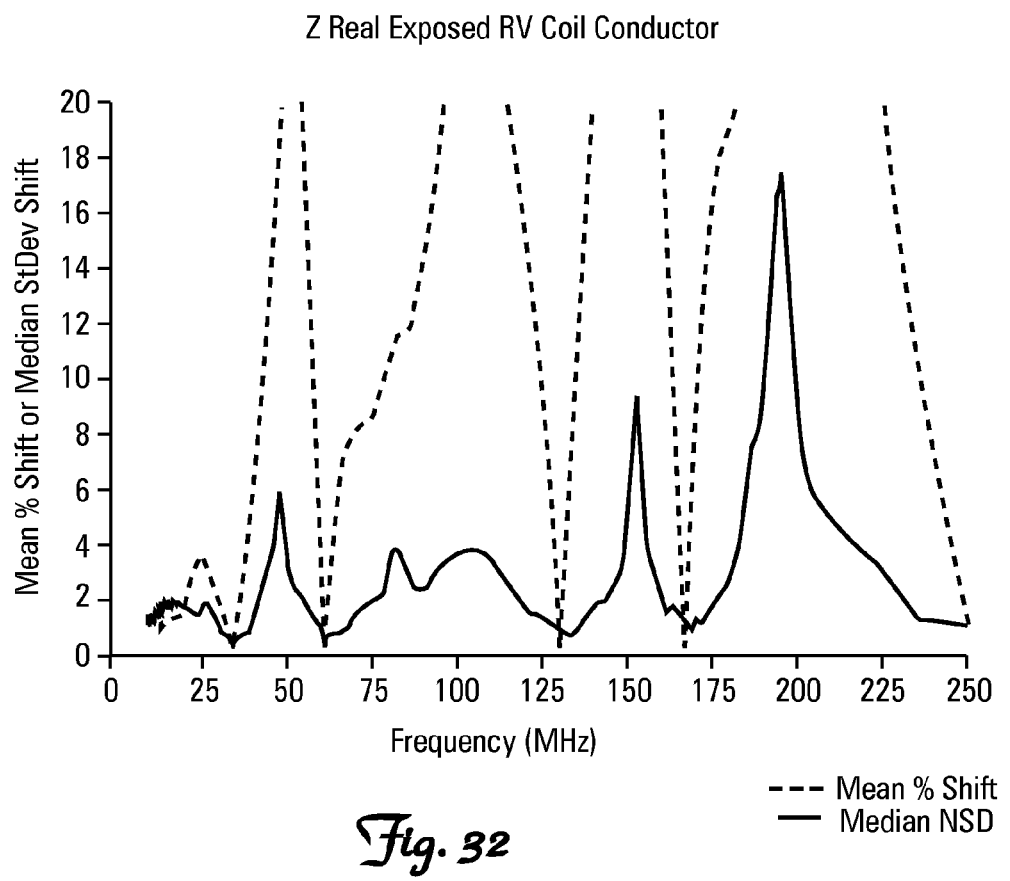
FIG. 32 illustrates the test results of changes in $Z_{real}$ with exposure from 0 MHz to 250 MHz on the RV coil conductor.
Figure 33:
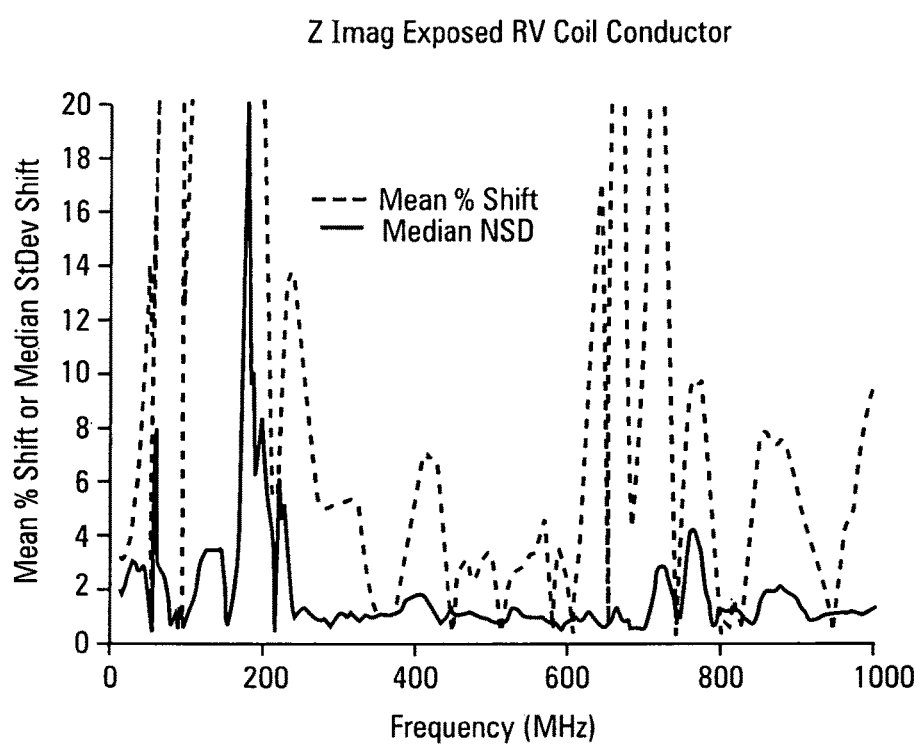
FIG. 33 illustrates the test results of changes in $Z_{imag}$ with exposure on the RV coil conductor.
Figure 34:
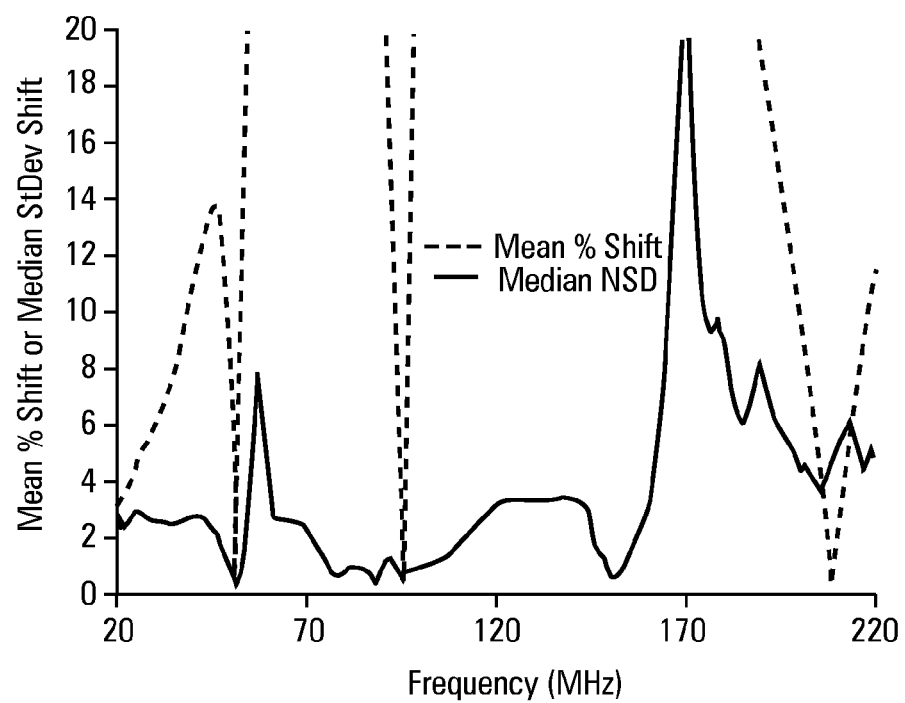
FIG. 34 illustrates the test results of changes in $Z_{imag}$ with exposure from 20 MHz to 220 MHz on the RV coil conductor.

As seen in FIG. 31, there are a number of $Z_{real}$ significant peaks extending out to 950 MHz. However, the lower frequency peaks are the most dramatic so the focus was trained on those. In particular, focus was on the usable peaks at 50 MHz, 155 MHz, and 200 MHz, which are shown zoomed in FIG. 32. Changes in $Z_{imag}$ were measured and as seen in FIG. 33, $Z_{imag}$ has many usable spectral peaks. There is an intriguing peak at approximately 775 MHz but it just reaches 4 sigma. However, in FIG. 34 (which is a portion of FIG. 33 zoomed), $Z_{imag}$ has a very broad peak at approximately 170 MHz that is >4 sigma from approximately 162 MHz to approximately 215 MHz. That breadth suggests a very robust and repeatable measurement parameter. There is also a usable peak for this embodiment at about 56 MHz.

Thus, based on testing results, it can be concluded that conductor 22 exposure can be detected with a high degree of confidence by noting changes in the $Z_{real}$ at approximately 200 MHz and $Z_{imag}$ at approximately 170 MHz.

Figure 35:
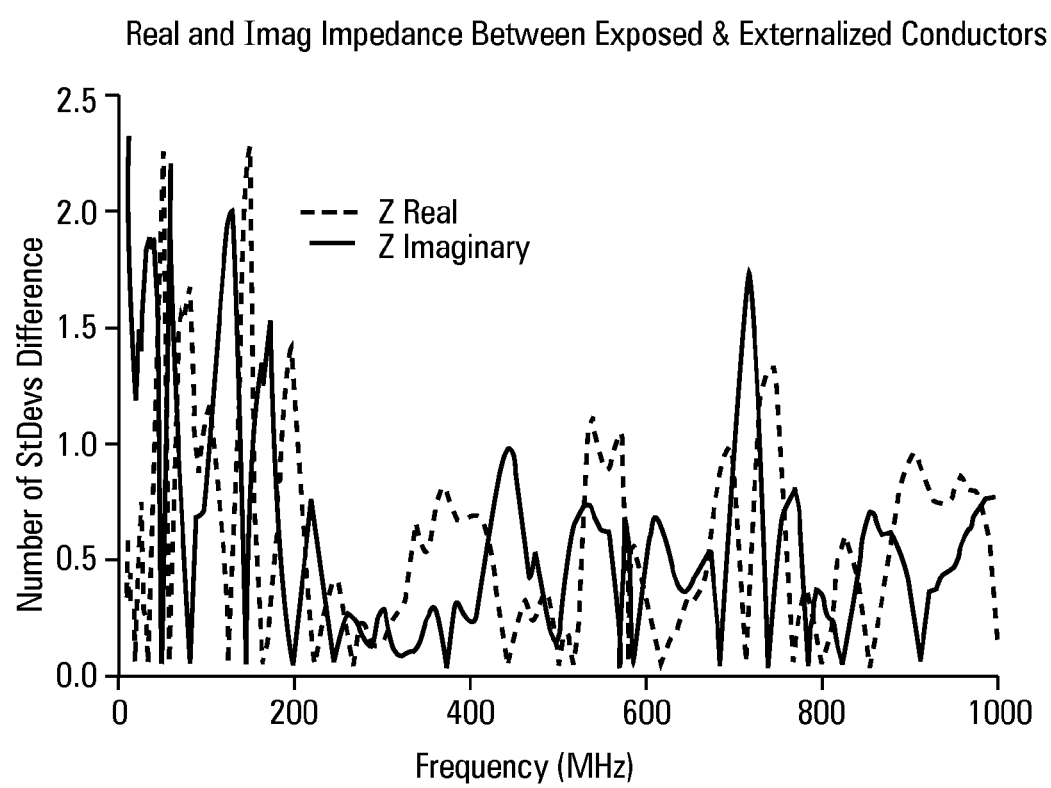
FIG. 35 illustrates the impedance spectrum difference between exposed and externalized on the RV coil conductors during testing.
Figure 36:
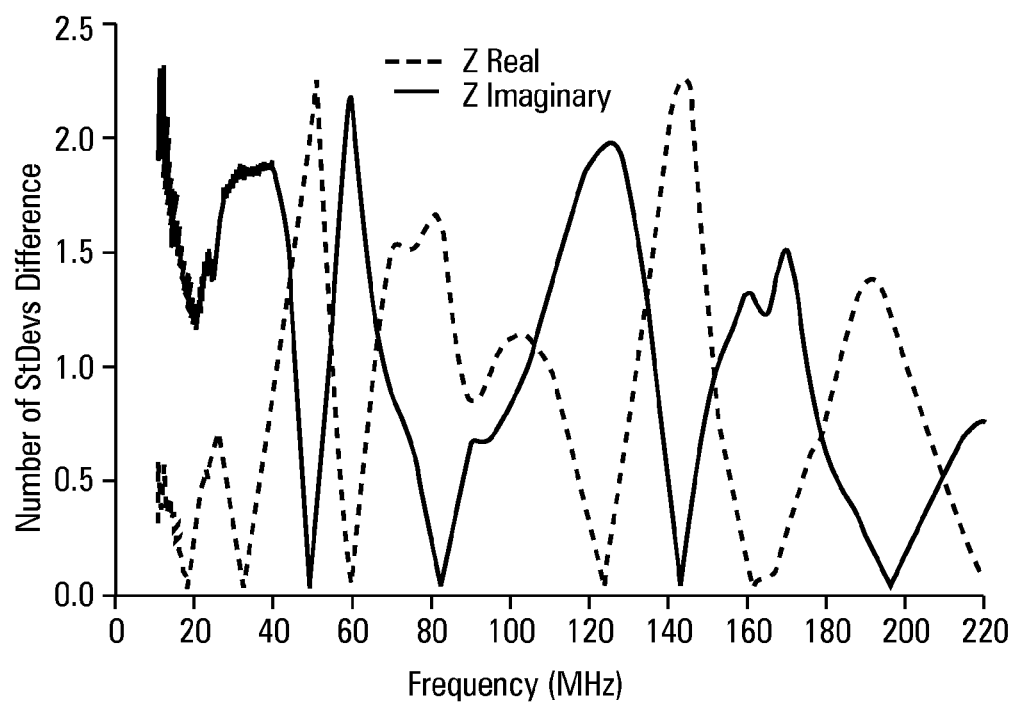
FIG. 36 illustrates the impedance spectrum difference between exposed and externalized RV coil conductors from 0 MHz to 220 MHz during testing.
Figure 37:
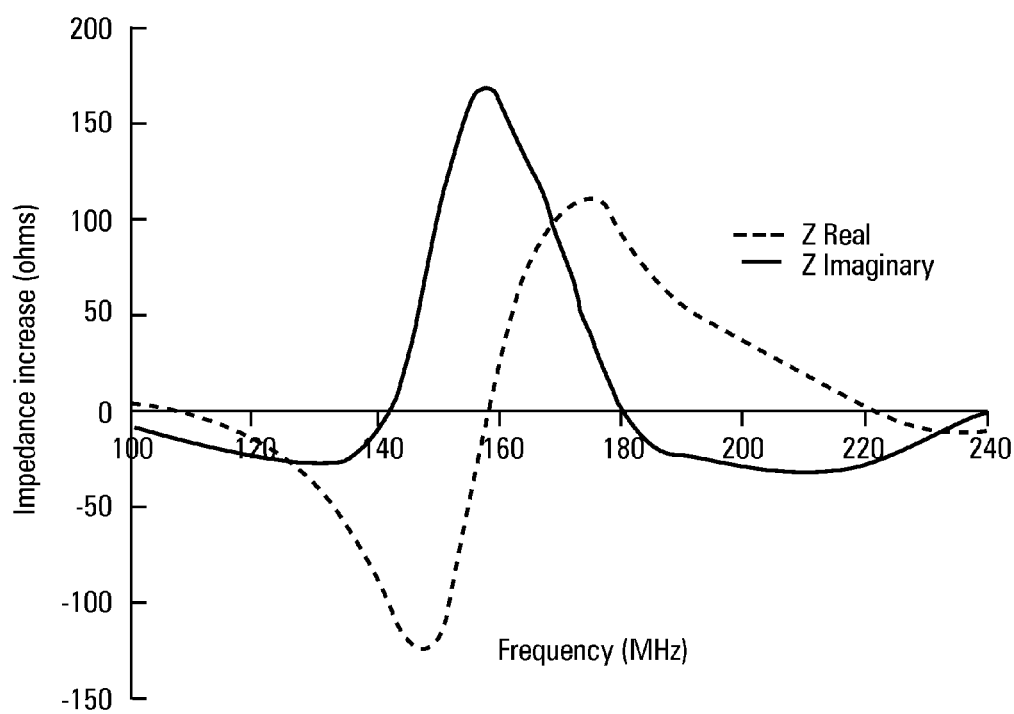
FIG. 37 illustrates the impedance shift with RV coil conductor exposure for Lead 10 during testing.
Figure 38:
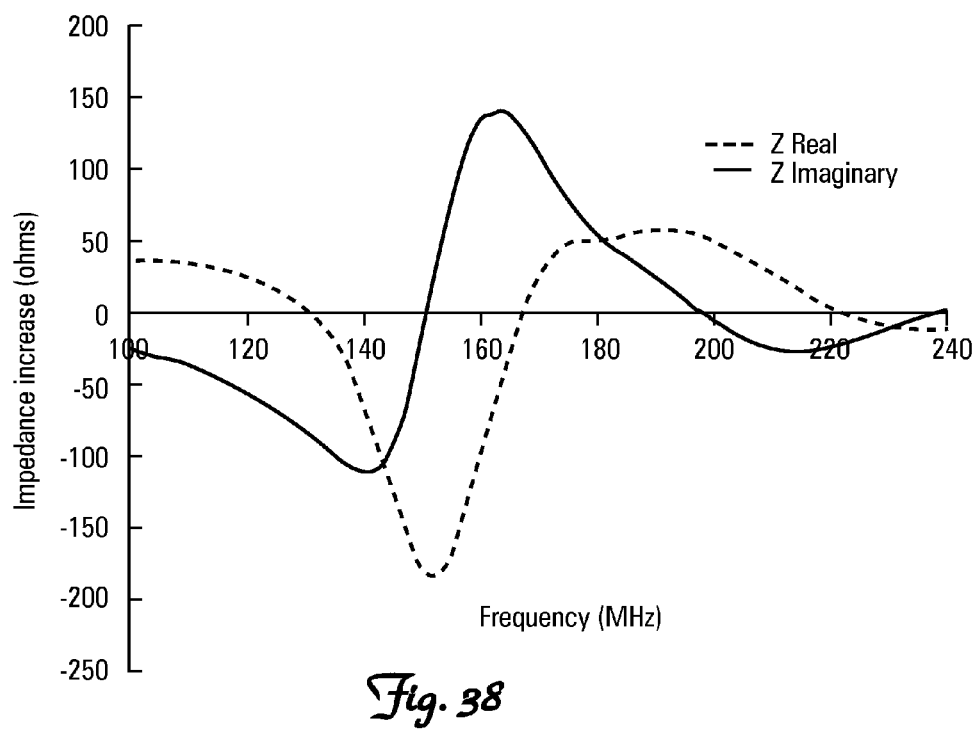
FIG. 38 illustrates the impedance shift with RV coil conductor exposure for Lead 11 during testing.
Figure 39:
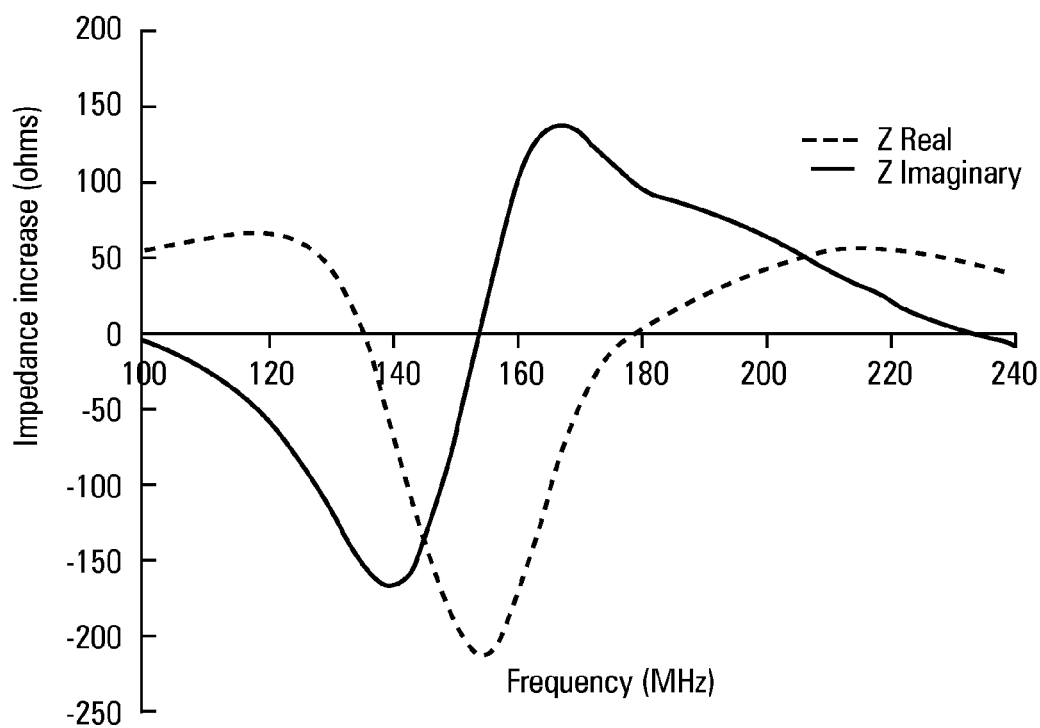
FIG. 39 illustrates the impedance shift with RV coil conductor exposure for Lead 12 during testing.
Figure 40:
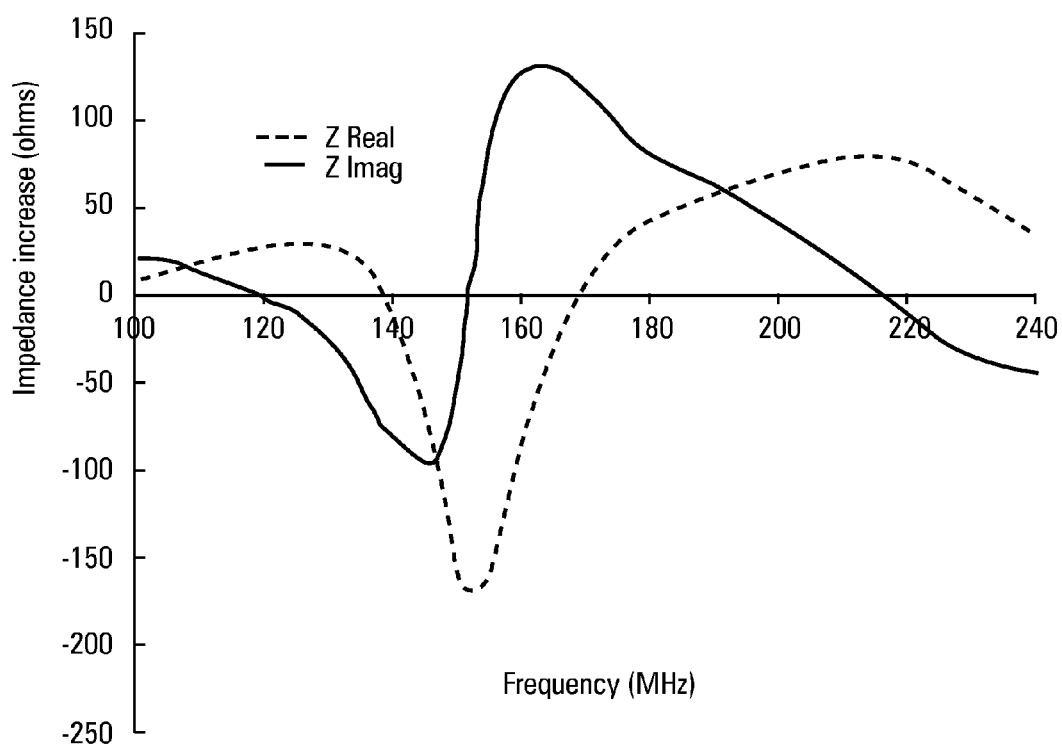
FIG. 40 illustrates the impedance shift with RV coil conductor exposure for Lead 13 during testing.
Figure 41:
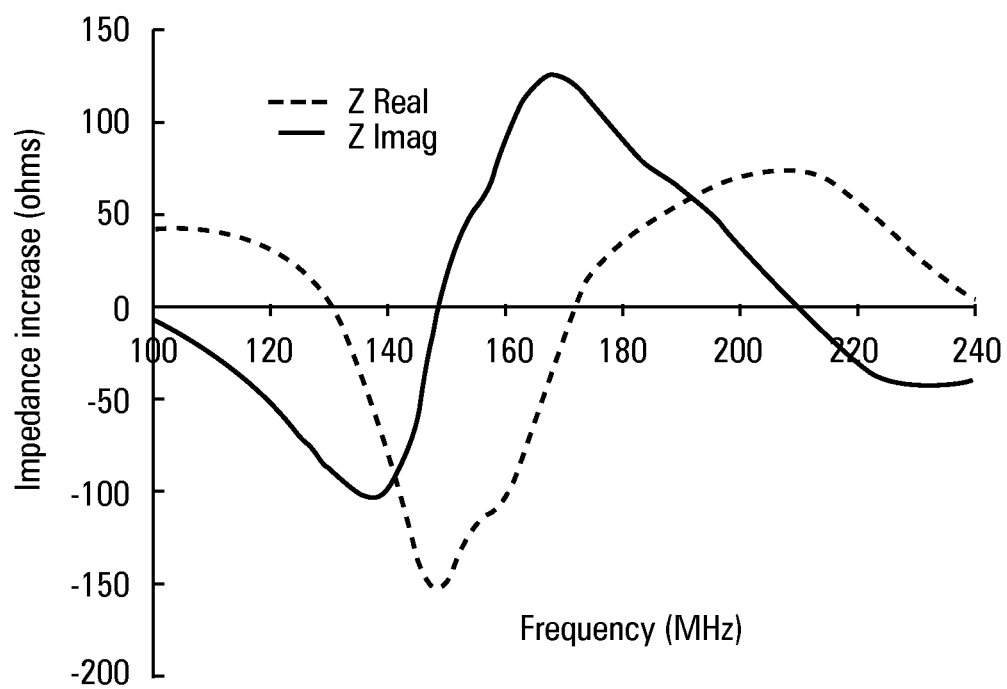
FIG. 41 illustrates the impedance shift with RV coil conductor exposure for Lead 14 during testing.

As shown in FIG. 35 and FIG. 36, the testing process further resulted in noting a subtle difference between exposed RV coil conductors 22 and externalized intact conductors 22. The largest difference appears to be at the lower frequency limit of 10 MHz which suggests that a lower RF frequency might be used. There are fairly broad peaks at 30 and 120 MHz, in $Z_{imag}$, of about 2 sigma. Thus, it is possible to differentiate, with the disclosed technique, between an exposed and merely externalized RV coil conductor 22.

FIGS. 37 to 41 are individual lead impedance spectral shifts with exposure for Leads 10 to 14 where a separate testing was done by performing a simple test of sweeping to find the minimum $Z_{imag}$. The spectral shifts are shown for 100 MHz to 300 MHz as these have the frequencies where the shifts are statistically significant. With the conductor 22 exposed there is an increase in $Z_{imag}$ at about 160 MHz and a drop in $Z_{real}$ at about 145 MHz.

FIG. 42 highlights the results where rather than focusing on a specific frequency, the frequencies from 100 MHz to 200 MHz were swept and the minimum value for $Z_{imag}$ was noted. $Z_{imag}$ runs negative for most of this band so the less negative value is sought. If that is less negative, i.e., >−290Ω, then a faulty RV coil conductor 22 can be diagnosed. Note that the $Z_{imag}$ increase is substantial with a range of 4.46 to 11.90 standard deviations.

Thus, based on these results, it can be concluded that conductor 22 exposure can be detected with a high degree of confidence by performing a simple test of sweeping to find the minimum $Z_{imag}$.

Third, the ring conductors 22 were externalized. FIG. 43 is a table that details the lead name, lead serial number, model number, and the distance from tip where the externalization was introduced.

Figure 44:
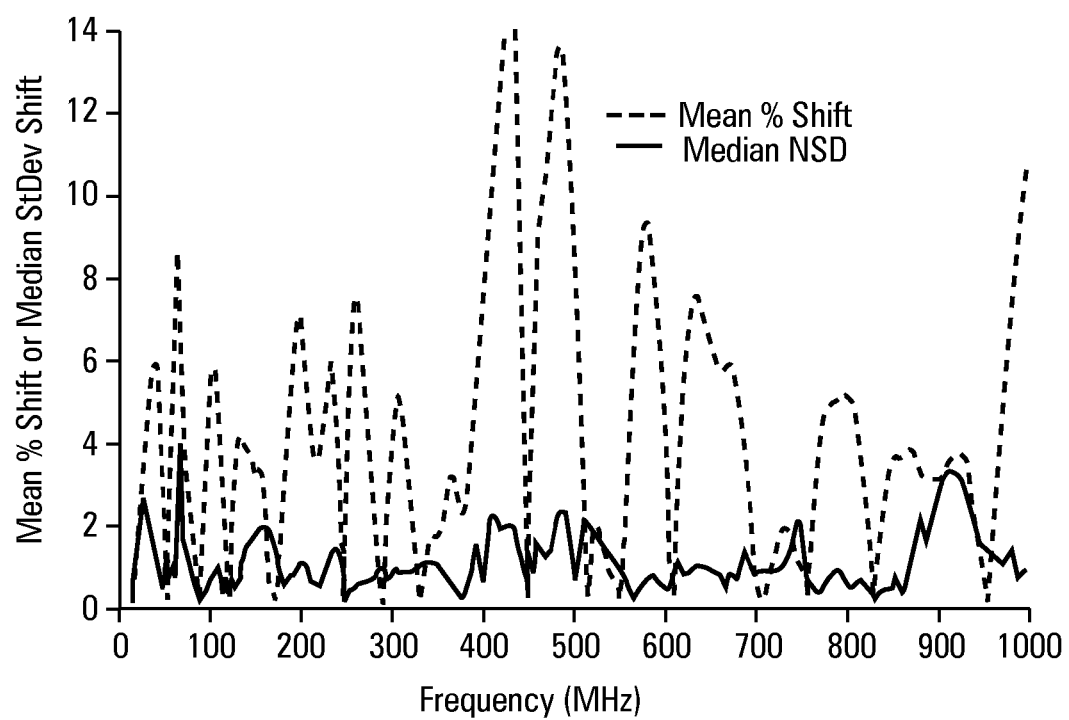
FIG. 44 illustrates the changes in $Z_{real}$ with externalization of a ring conductor during testing.

The $Z_{mean}$ shift was calculated for all 5 leads. Also the number of standard deviations (NSD) of shift was calculated for each lead at each frequency. The standard deviation was determined from the 5 leads before modifications. As seen in FIG. 44, there were 2 peaks with 4 and 3-sigma shifts. These peaks each had shifts of 8% and 3%, which were not high.

Figure 45:
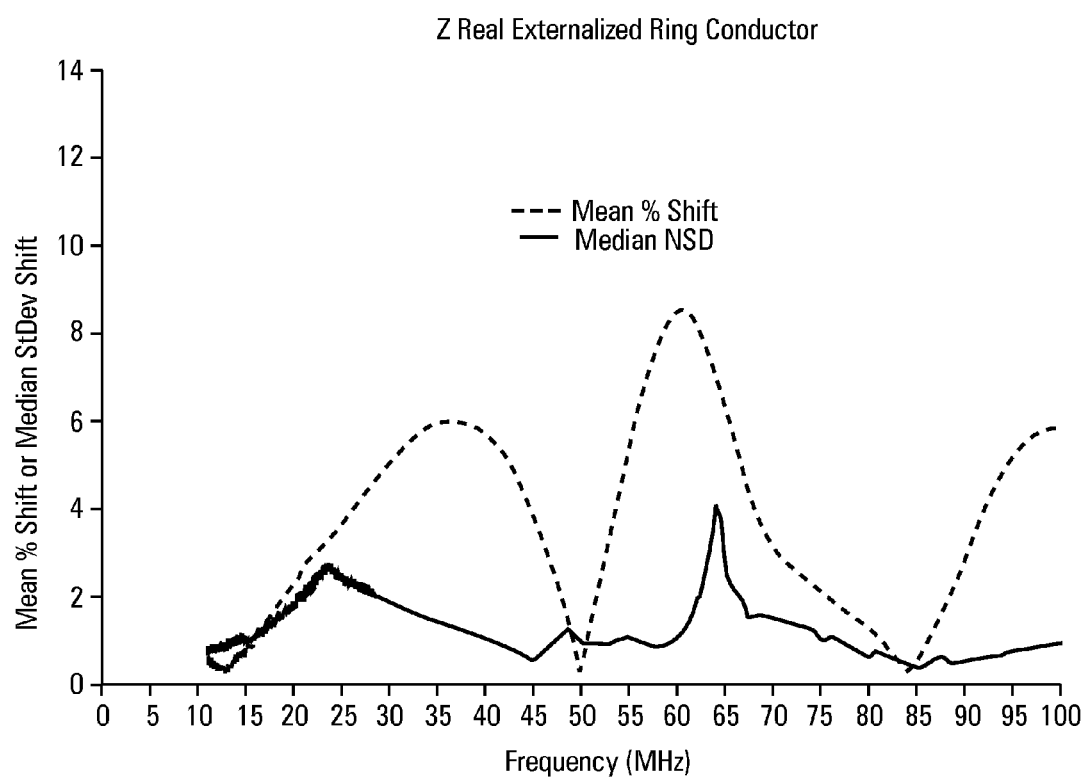
FIG. 45 illustrates the changes in $Z_{real}$ with externalization of a ring conductor from 10 MHz to 100 MHz during testing.
Figure 46:
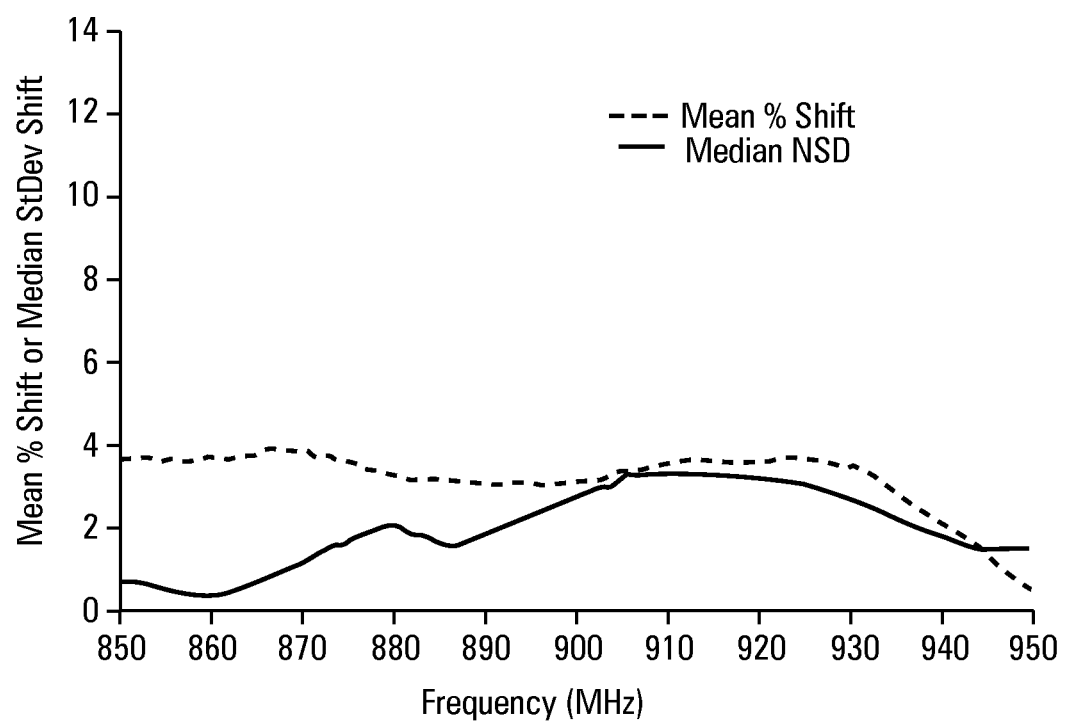
FIG. 46 illustrates the $Z_{real}$ high frequency impedance from 850 MHz to 950 MHz on an externalized ring conductor during testing.

As seen in FIG. 45, the peak at 65 MHz is not robust having a 4-sigma shift. It is also fairly narrow thus raising the possibility that it could be noise from multiple comparisons. There is a subtle "peak" at 910 MHz (see FIG. 46) of 3 sigma. However, since it is fairly wide (>2 sigma from 890-935 MHz) it can represent a true shift.

Figure 47:
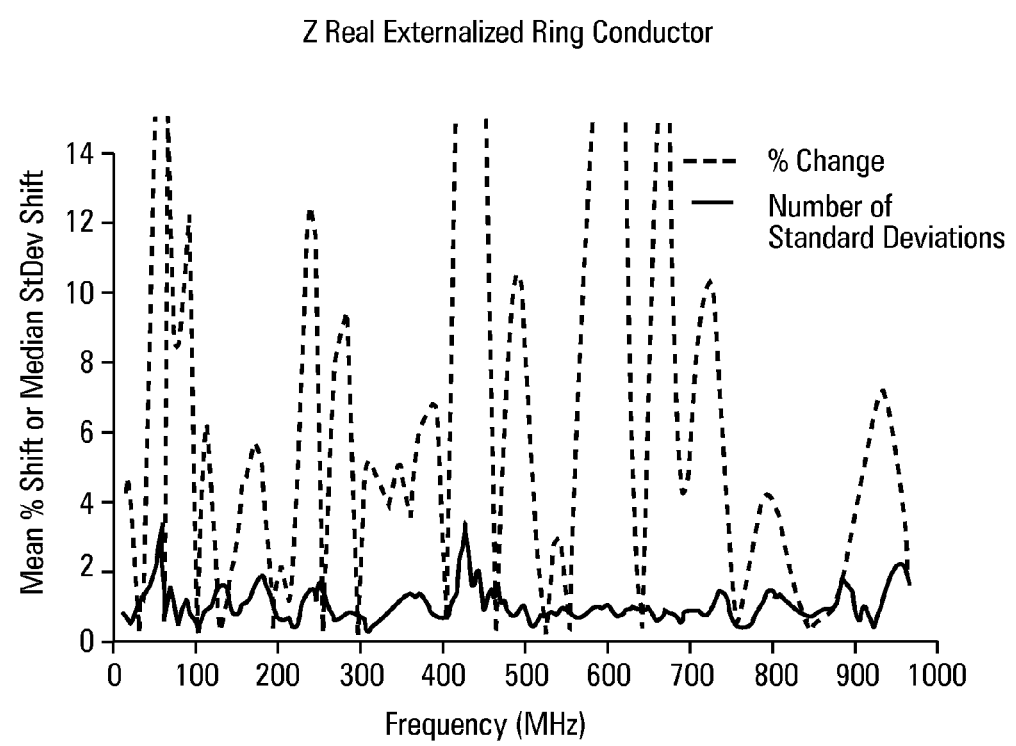
FIG. 47 illustrates the changes in $Z_{imag}$ with externalization of a ring conductor during testing.
Figure 48:
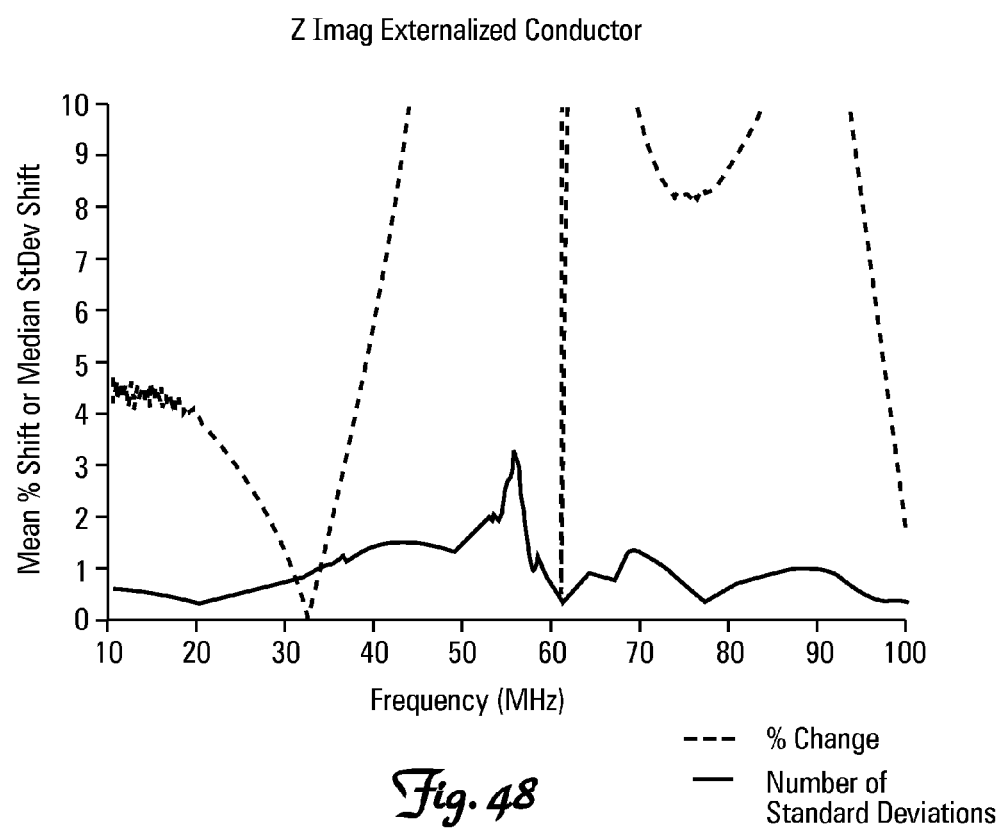
FIG. 48 illustrates the changes in $Z_{imag}$ with externalization of a ring conductor from 10 MHz to 100 MHz during testing.
Figure 49:
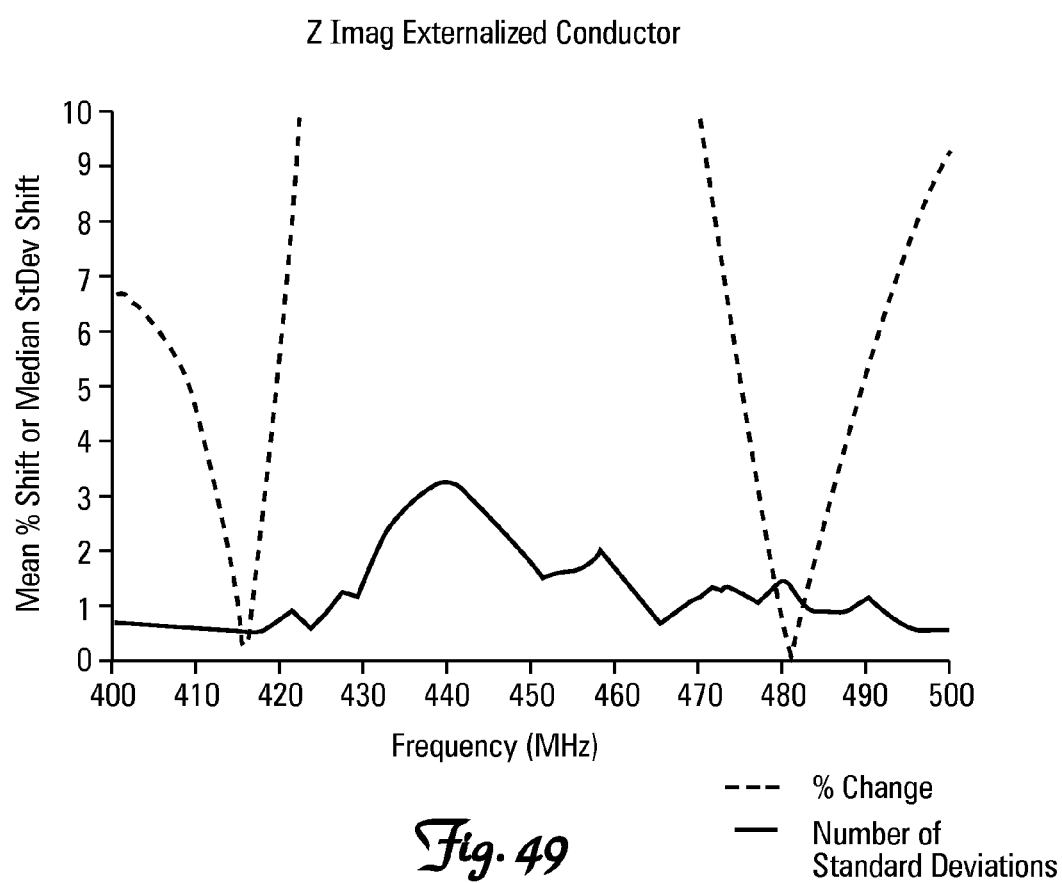
FIG. 49 illustrates the changes in $Z_{imag}$ with externalization of a ring conductor from 400 MHz to 500 MHz during testing.

As seen in FIG. 47, there are 2 peaks in the $Z_{imag}$ response at about 50 MHz and about 450 MHz. While each are only about 3 sigma they represent large value shifts (>>10%) and as such, represent genuine changes. The first low frequency peak is seen zoomed in FIG. 48 and has a peak of 3.2 sigma at about 56 MHz. The second low frequency peak is seen zoomed in FIG. 49 and has a peak of 3.2 sigma at 440 MHz with a very large value shift.

It is concluded that externalization of the ring conductor 22 can be detected by noting changes in the $Z_{real}$ at about 65 MHz and about 910 MHz and $Z_{imag}$ at about 56 MHz and about 440 MHz. The differences are more subtle than those seen with externalization of the RV coil conductor 22.

Figure 50:
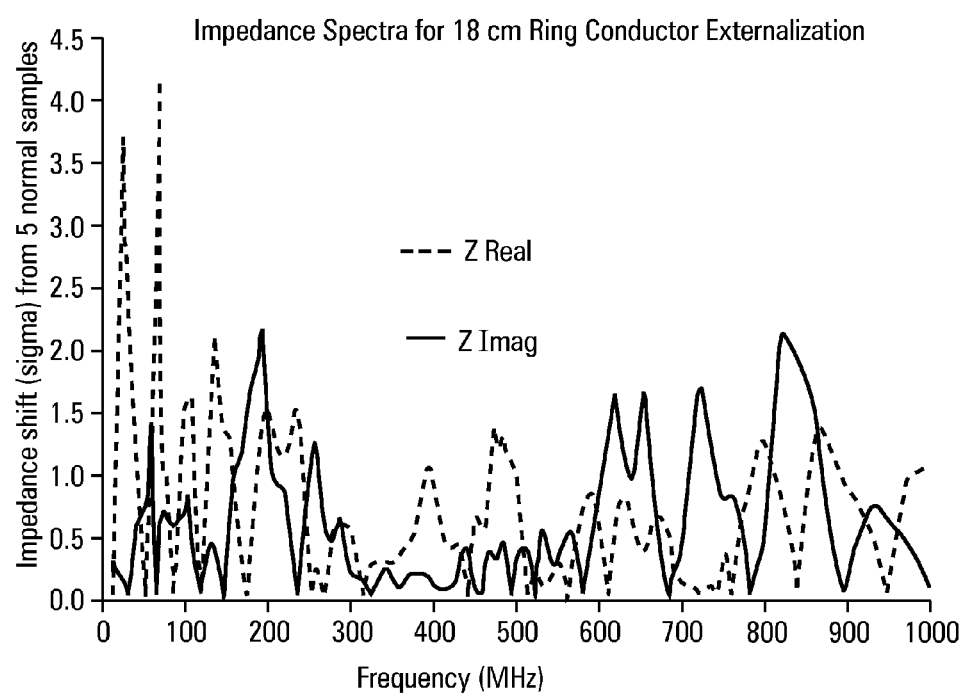
FIG. 50 illustrates the testing results for the real and imaginary spectra for the 18 cm ring conductor externalization.
Figure 51:
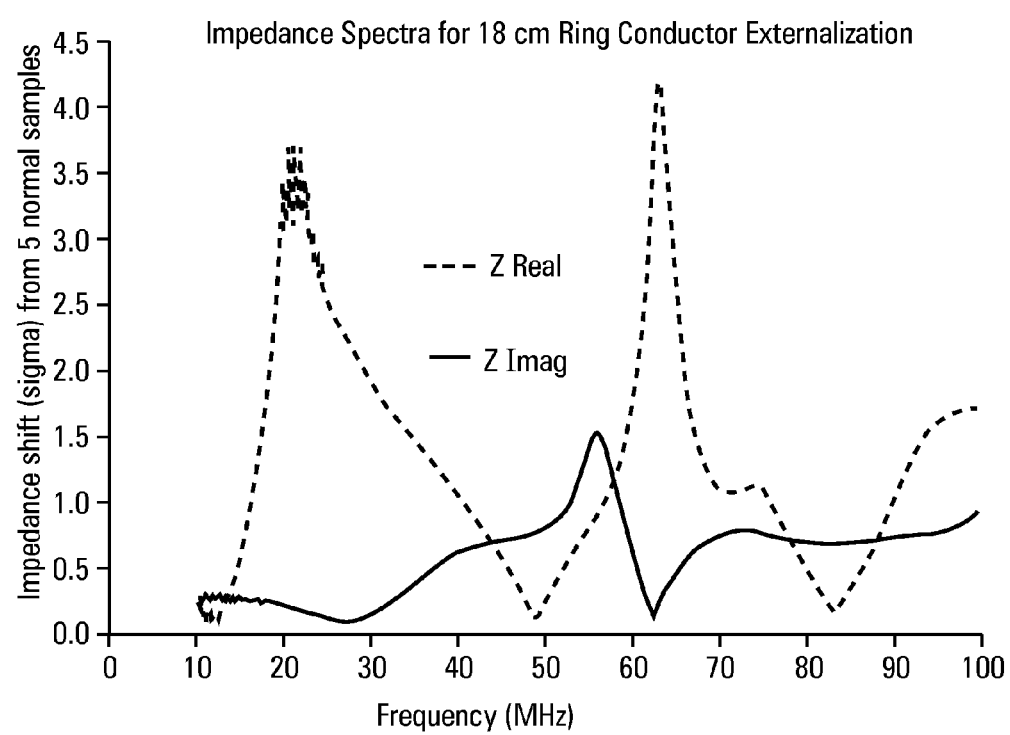
FIG. 51 illustrates the testing results for the real and imaginary spectra for the 18 cm ring conductor externalization from 10 MHz to 100 MHz.

Another analysis was performed on leads 10, 12, and 14 which had the externalization at 18 cm from the tip. This additional analysis was performed to determine if the subtle changes involved with ring conductor 22 externalization were affected by the consolidation of the 9 cm and 18 cm location data. FIG. 50 illustrates the real and imaginary spectra for just the 18 cm ring conductor externalization. As seen in FIG. 51, this analysis at 18 cm produced a stronger and wider peak in the real impedance at about 21 MHz. Note that the earlier peak at 65 MHz is still here almost unchanged. That may be a marker for a ring conductor 22 externalization anywhere.

However, the strong and wide peak at 21 MHz may be unique to an externalization location near 18 cm from the tip. Recall that the sampling was done with logarithmic frequency iterations. Thus, there are as many samples from 10-100 MHz as there are from 100-1000 MHz.

The peak at 21 MHz has about 500 samples where the shift is ≥2 sigma. That is 10% of the overall 5000 samples. Thus, a ring conductor 22 externalization, at 18 cm, can be detected.

Figure 52:
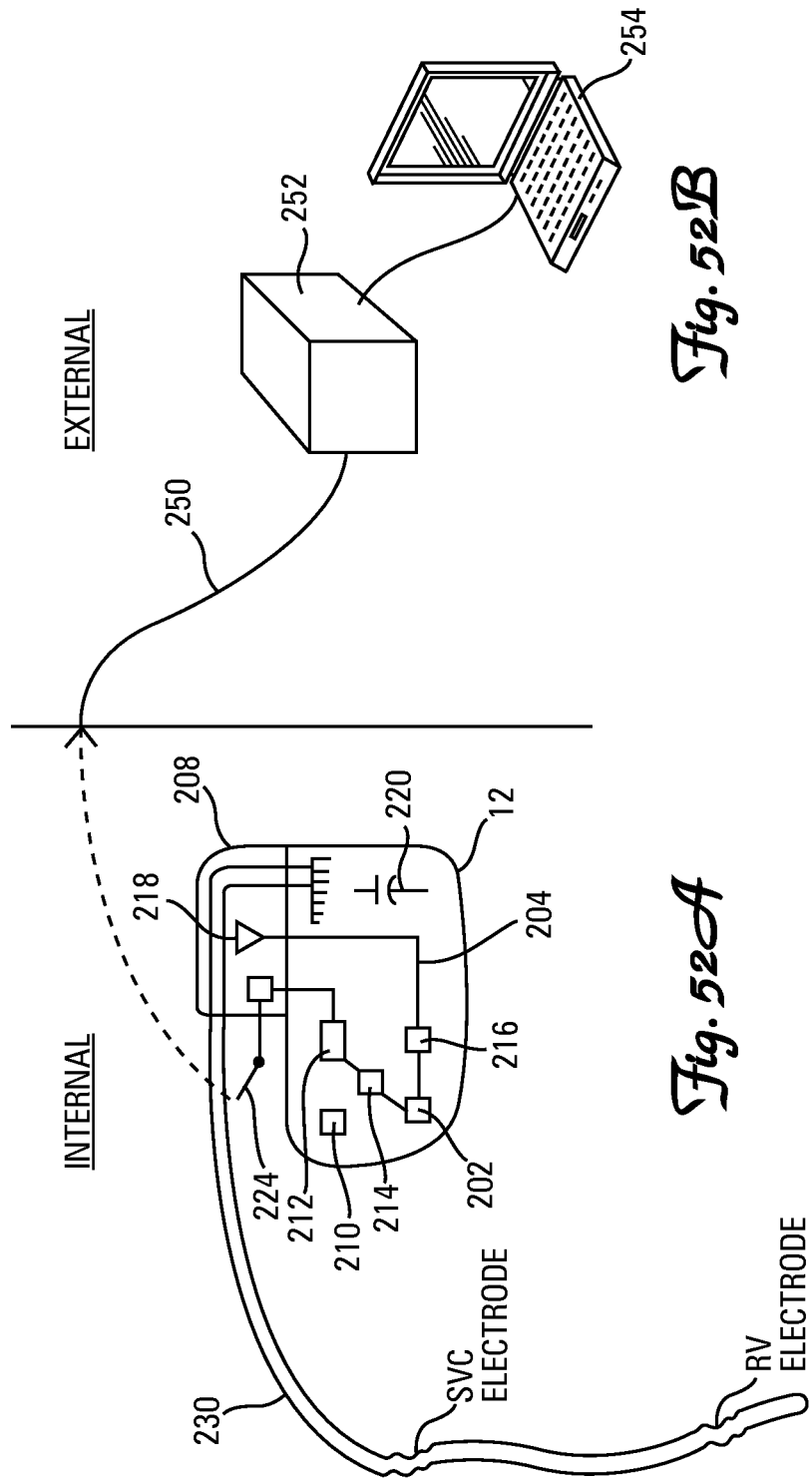
FIG. 52A is a block diagram of a system for internally analyzing an implantable cardiac lead within an ICD.
FIG. 52B is a block diagram of a system for externally analyzing an implantable cardiac lead outside of an ICD

FIG. 52A depicts an implantable cardiac lead system that can utilize an ICD pulse generator 200, for example, having a crystal frequency oscillator 202 used in methods of internally detecting conductor migration, damage, insulation abrasion or externalization within an implantable cardiac lead. In some embodiments, the crystal frequency oscillator 202 is also utilized for radio frequency communications 204 by the ICD 12. In embodiments, the crystal frequency oscillator 202 can be used to generate a high frequency test signal(s) for use in accordance with various embodiments as described. In one embodiment, a single target high frequency signal is used to conduct a rough evaluation of the imaginary impedance. For example, in an embodiment and referring to FIG. 52A, ICD 12 can include within ICD body 206, a microprocessor 210, a high-frequency signal source component 212, an oscillator 202, a radio frequency component 216 operably coupled to a radio antenna 218, and a high voltage therapy capacitor system 220. The high voltage therapy capacitor system 220 is conventional and is coupled to lead connectors 230 in ICD header 208 by a high frequency capacitor filter/isolation arrangement. In this embodiment, a frequency divider 214 is operably coupled between the oscillator 202 and the high-frequency signal component 212 that is controlled by the microprocessor 210. In this embodiment, the oscillator 202 is configured to provide the frequency for RF communications, for example, using the MICS band between 401 MHz and 406 MHz, and the frequency divider 214 is configured with flip-flops, for example, to divide this frequency down to a frequency between 100 MHz and 200 MHz that may be utilized in accordance with the various embodiments. A high-frequency test pulse can be commanded along the cardiac lead by the microprocessor 210 through the high-frequency component 212, and a switch arrangement 224.

If the rough evaluation of the imaginary impedance in response to the high frequency test signal generated internally within the ICD 200 indicates a deviation from an expected value, further testing and evaluation can be indicated to be performed, for example, by an external system such as shown in FIG. 52B. If the rough evaluation indicates a deviation, the lead system 230 can be exposed and connected by an adapter cable 250 to a high frequency signal source generator 252 that is external to the ICD 12. In embodiments, the pre-indication analyzed from the source signals within the ICD 12 can be further analyzed by any of the various sweep frequency band methods utilizing pulse generators external to, for example, ICD 12. For example, the cardiac lead can be operably coupled with an adapter cable 250 to an external signal generator after a rough, pre-indication of imaginary impedance from the source signals within the ICD 12 is greater than expected.

For example, in an embodiment and referring to FIG. 52B, the external high frequency pulse generator may comprise a laptop 254 or other computing device, an external signal source 252, and an adapter cable 250. The adapter cable 250 can be configured to operably couple to the cardiac lead in order to provide signals, as described in the myriad methods above, along the cardiac lead. In embodiments, the laptop 254 is operably coupled to and configured to control the external signal source 252. In other embodiments, the external signal source 252 can provide its own signal output configuration.

Figure 53:
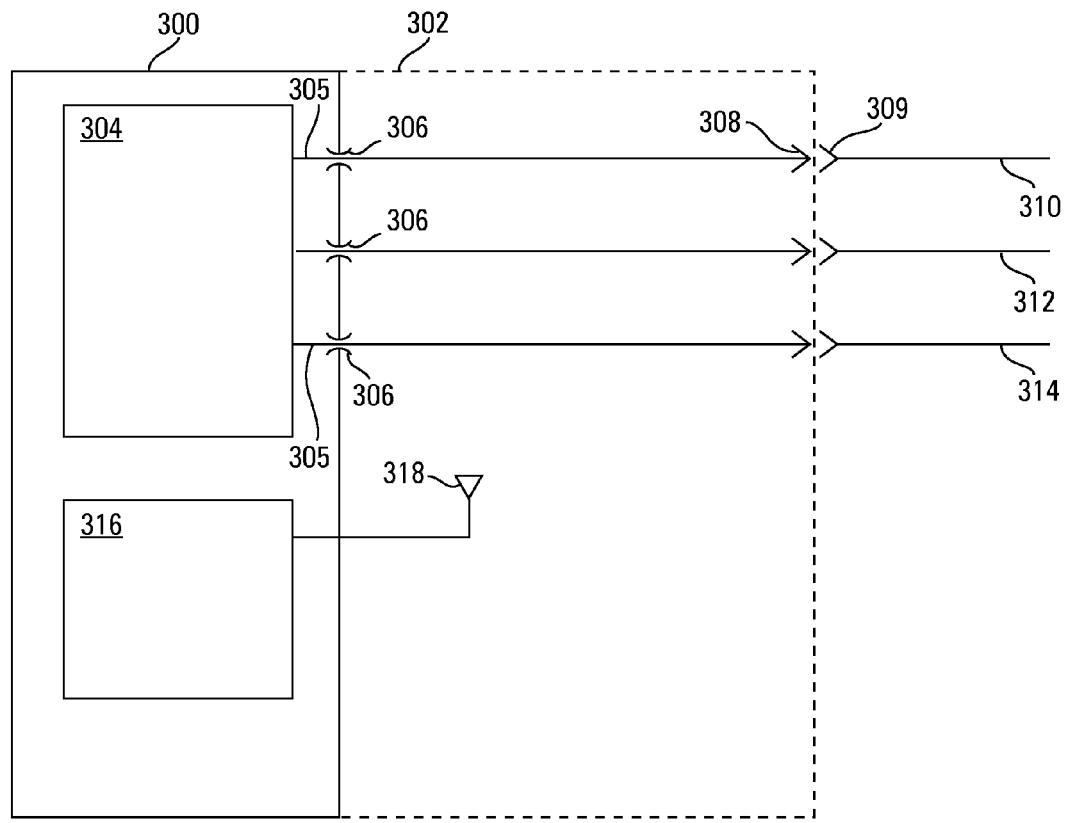
FIG. 53 illustrates a conventional housing and header circuitry for an ICD.

FIG. 53 depicts the typical header circuitry of an ICD 12. The header 300 having therapy circuitry 304, RF circuitry 316. The header 300 further has a plurality of apertures adjacent the polymer non-conductive header 302 through which electrical leads 305 pass carrying electrical signals. The signals traditionally pass thru feed thru capacitors 306 which are typically about 1 nF and designed to block interference such as mobile phone signals. The signal is then delivered to the connectors 308 which are securely fastened to the proximal conductor tips 309 of the tip conductor 310, the ring conductor 312 and the RV coil conductor 314 of the implantable lead. Since the feed thru capacitors block RF signals, the RF circuitry 316 uses an unfiltered opening to pass its signal to and from the antenna 318 in the header 302. Various methods of delivering the RF signal to and from the header are taught in U.S. Patent Publication No. 2008/0039898 to Lim, U.S. Patent Publication No. 2008/0021522 to Verhoef, U.S. Patent Publication No. 2010/0204759 to Chapman, and U.S. Patent Publication No. 2010/0168818 to Barror. In some of these teachings (e.g., Barror) the RF circuitry is placed in the header. The embodiments herein are meant to include such an approach and are not meant to be limited to the embodiments shown with the RF circuitry limited within the titanium housing.

Figure 54:
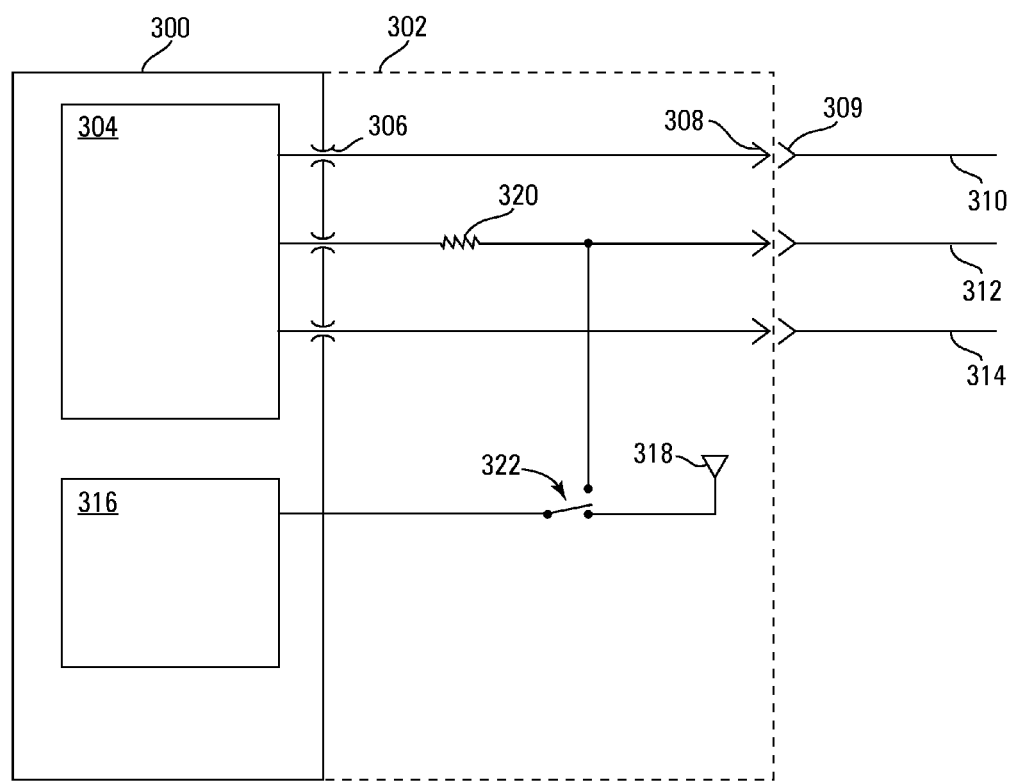
FIG. 54 illustrates the header circuitry for deriving the impedance measurements of the ring conductor according to an embodiment.

FIG. 54 depicts an embodiment for testing the impedance spectra (real and imaginary) of the ring conductor 312. Resistor 320 is inserted in series with the ring conductor 312 (equivalently with the tip conductor) and has a value of about 200Ω In other embodiments, ranges of 100Ω to 1000Ω are acceptable. The resistor must be large enough to prevent the feedthru capacitor 306 from shunting the RF impedance test signal yet not so large that it interferes with bipolar pacing by absorbing too much of the pacing energy. A switch 322 then selects between connecting the RF signal to the antenna 318 or the ring conductor 312. As discussed above, the RF circuitry is modified to perform impedance testing as well as the conventional RF communications. Switch 322 can be an Analog Devices ADG 318 which is capable of passing signals up to 1.0 GHz. Switch 322 requires a power connection to the inner housing for its 1.65-2.75 V single power requirements (not shown).

In another embodiment, the switch 322 can be a magnetic reed transfer switch such as the ORT551 or KSK-1C90F available from Meder Electronics. The reed switch is the preferred switch for applications where the impedance testing is done during follow-up clinic visits or where a patient can be expected to place a magnet over the ICD on a scheduled basis to perform the testing. In embodiments, the invention anticipates that sophisticated electrogram analysis might detect a possible lead malfunction and reports this to a remote monitoring service. The patient would then be instructed to place the magnet over the device to perform the impedance testing.

Figure 55:
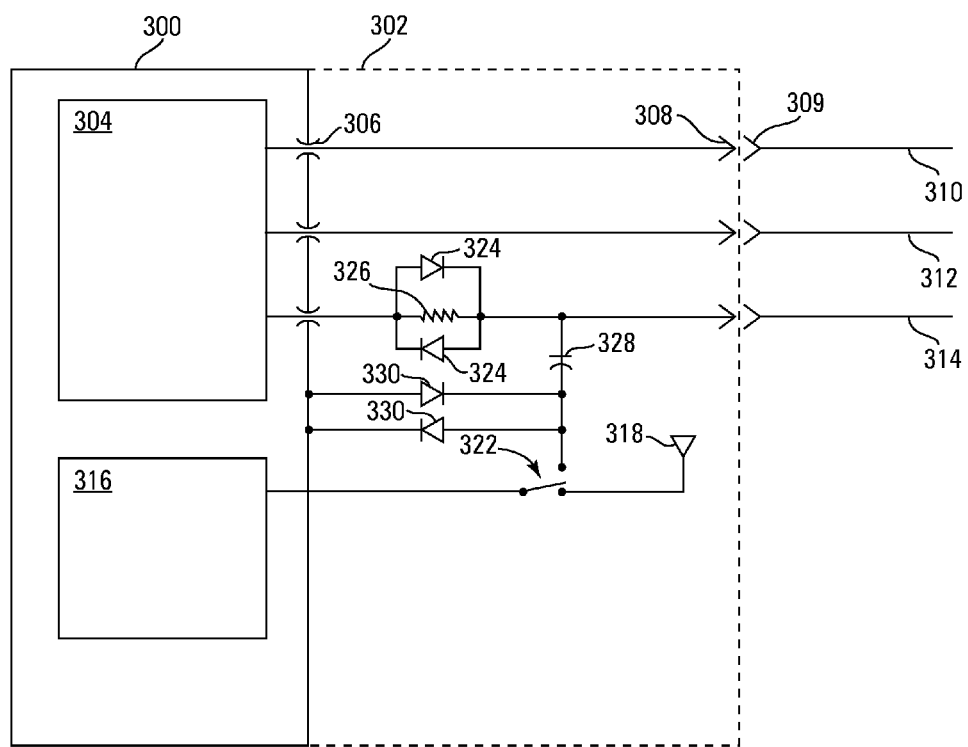
FIG. 55 illustrates the header circuitry for deriving the impedance measurements of the RV coil conductor according to an embodiment.

FIG. 55 depicts the related circuitry for testing the impedance spectra of the RV coil conductor 314 (equivalently an SVC coil conductor). Switch 322 functions as described above. Resistor 326 delivers low-voltage signals for possible pacing and electrogram analysis and recording. Resistor 326 also isolates the RF signal from the feedthru capacitor 306 as discussed above. Since the RV coil is generally not used for pacing, the resistor value could be higher than 1 kΩ and the acceptable range is 100Ω to 10 kΩ. In an embodiment, the resistor value can be 200Ω. The high-current shock is delivered thru the anti-parallel diodes 324. These can be of the 1N4007 type as the diodes 324 are rated to handle the peak 30. A currents of defibrillation and withstand 1 kV. The diode 324 voltage drop of about 0.7 V is insignificant compared to the 900 V defibrillation shock. The diodes 324 have a capacitance of about 20 pF and thus they will not interfere with high-frequency impedance spectral measurements. Importantly, with an impedance testing signal of <400 mV peak-to-peak the diodes 324 will not conduct and interfere with high-frequency impedance spectral measurements.

For the RV coil testing the situation is more complicated (compared to the ring conductor testing) as the high voltage could damage the RF circuitry. Capacitor 328 serves to pass the high-frequency signals but to largely block the 900 V defibrillation shock. The four edges of the 900 V defibrillation shock will generate short current spikes (=Cdv/dt) thru the capacitor 328 and those will be absorbed by the anti-parallel diodes 330. Capacitor 328 can have a range of 0.3 nF to 3.0 nF. In an embodiment, capacitor has a rating of 1.0 nF.

Figure 56:
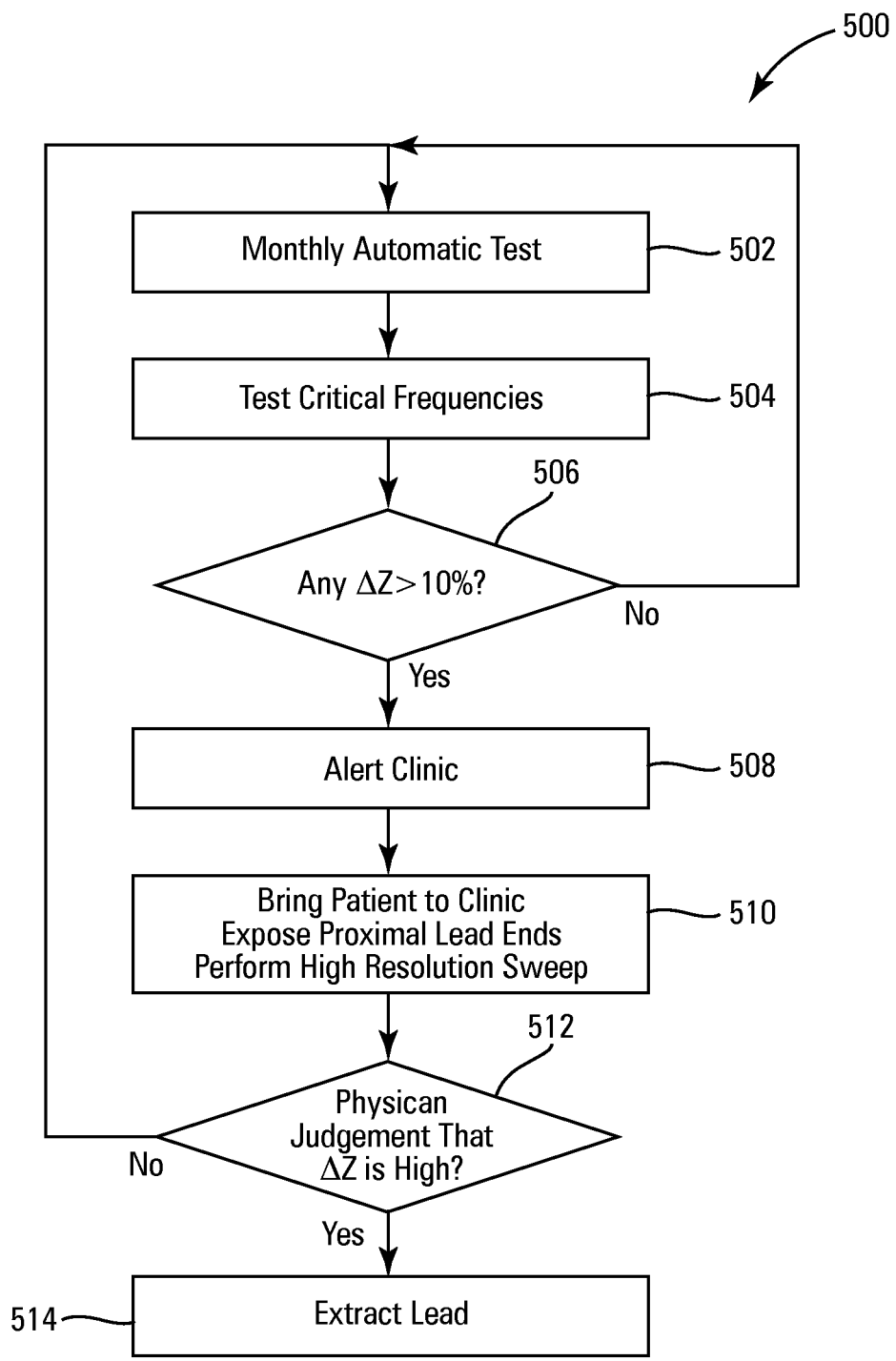
FIG. 56 is a flowchart illustrating a method of the imaginary impedance test at a high level for the various embodiments.

FIG. 56 is a flowchart illustrating a method of the imaginary impedance test at a high level 500 for the various embodiments. Imaginary impedance testing is automatically performed at monthly intervals at step 502 in one embodiment. In other embodiments, testing can be performed at other regular intervals, e.g., daily, weekly, bi-weekly, every other month, etc. The critical frequencies, as previously established are tested at 504. The imaginary impedances are analyzed and it is determined at 506 if any measurement of the imaginary impedance exceeds a predetermined threshold, such as 10 percent. If the imaginary impedance is within acceptable levels (<10%), then no action is taken until the next scheduled interval testing 502. If the imaginary impedance is not within acceptable levels, the clinic is alerted 508. The patient is then brought in for further testing at the clinic location which may involve exposing the proximal lead ends of the cardiac lead and performing the high resolution sweep 510 as outlined in the various embodiments described above. The physician determines if the imaginary impedance is too high at 512 and if so, the lead may be extracted at 514. Otherwise, no remedial action is taken until the next scheduled interval testing 502, although the physician may determine that the periods for testing and/or the thresholds for reporting should be modified.

Figure 57:
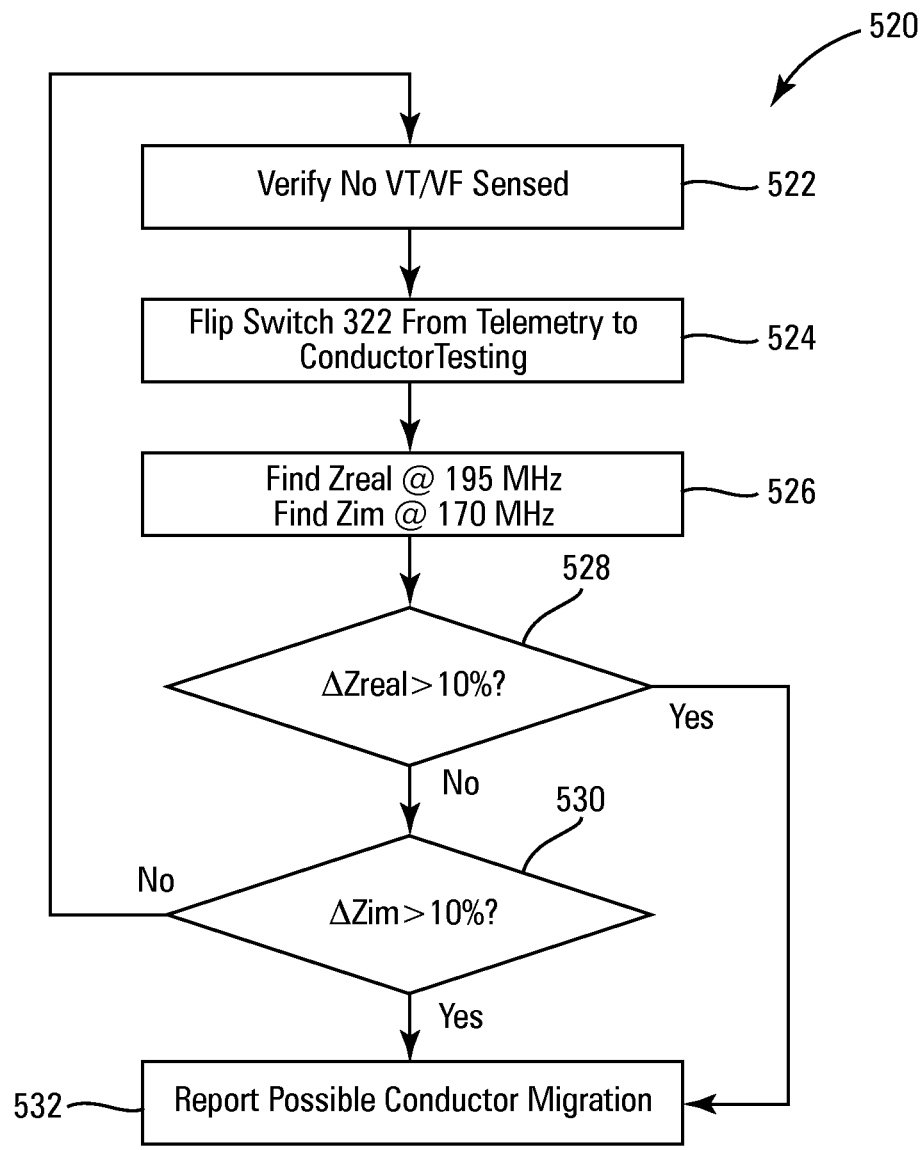
FIG. 57 is a flowchart illustrating a method of the imaginary impedance test of the RV coil conductor according to an embodiment.

FIG. 57 is a flowchart illustrating a method of the imaginary impedance test of the RV coil conductor 520 according to the embodiment using the circuitry of FIG. 55. To begin, it is verified at 522 that no ventricular tachycardia or ventricular fibrillation is sensed. If neither is sensed, then the switch 322 (FIG. 55) is flipped to switch from telemetry function to conductor testing function at 524. Testing is performed, as detailed above, and in one embodiment, changes are noted in the $Z_{real}$ at 195 MHz and $Z_{imag}$ at 170 MHz 526. In other embodiments, other frequency bands may be used. $Z_{real}$ is analyzed 528 and if greater than a predetermined threshold, such as 10%, then possible conductor migration is reported at 532. If $Z_{real}$ is less than a predetermined threshold, such as 10%, then $Z_{imag}$ analyzed at 530. In this embodiment, if $Z_{imag}$ is greater than 10%, conductor migration is reported at 532, otherwise the process is reset until the next test cycle begins over at 522.

Figure 58:
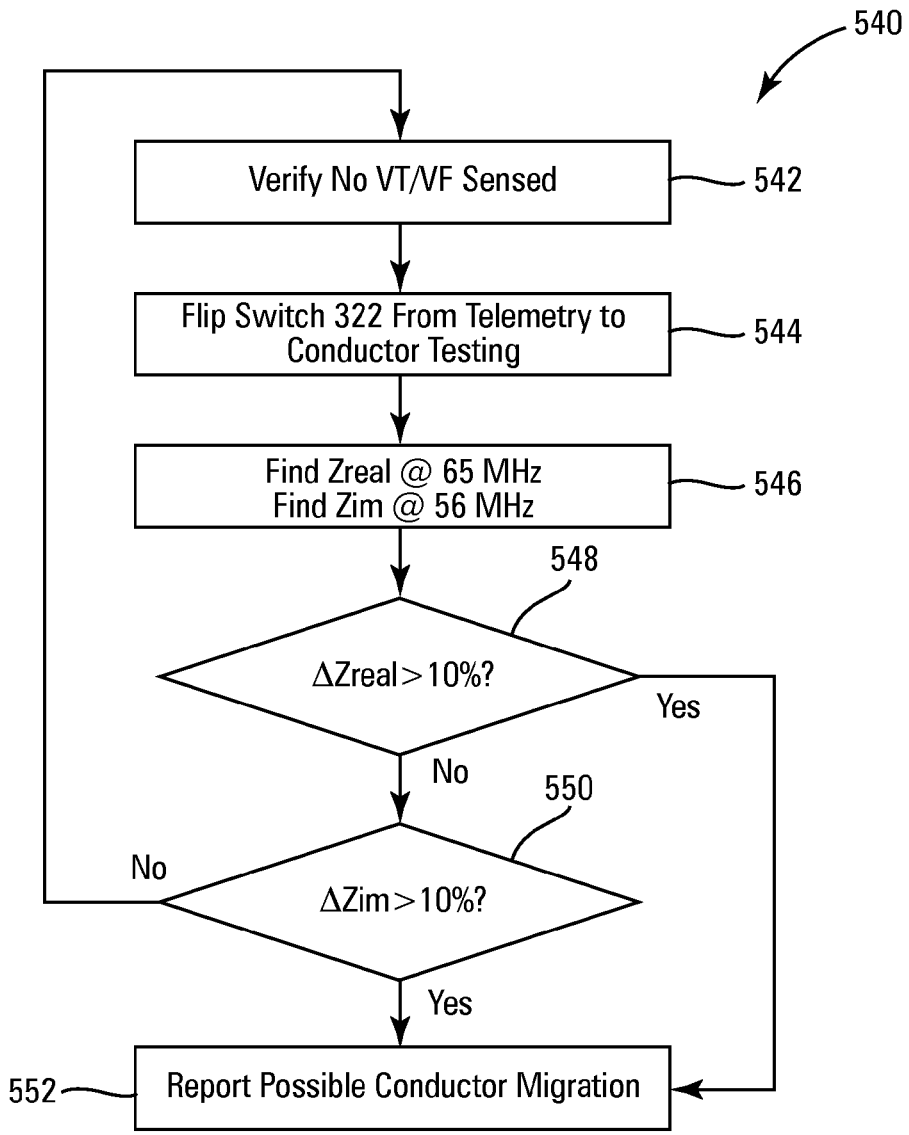
FIG. 58 is a flowchart illustrating a method of the imaginary impedance test of the ring conductor according to an embodiment.

FIG. 58 is a flowchart illustrating a method of the imaginary impedance test of the ring conductor 540 according to an embodiment using the circuitry of FIG. 540. To begin, it is verified at 542 that no ventricular tachycardia or ventricular fibrillation is sensed. If neither is sensed, then the switch 322 (FIG. 54) is flipped to switch from telemetry function to conductor testing function at 544. Testing is performed, as detailed above, and in one embodiment, changes are noted at 546 in the $Z_{real}$ at 65 MHz and $Z_{imag}$ at 56 MHz. In other embodiments, other frequency bands may be used. $Z_{real}$ is analyzed at 548 and if greater than a predetermined threshold, such as 10%, then possible conductor migration is reported at 552. If $Z_{real}$ is less than a predetermined threshold, such as 10% then $Z_{imag}$ analyzed at 550. In this embodiment, if $Z_{imag}$ is greater than 10%, conductor migration is reported at 552, otherwise the process is reset until the next test cycle begins over at 542.

Figure 59:
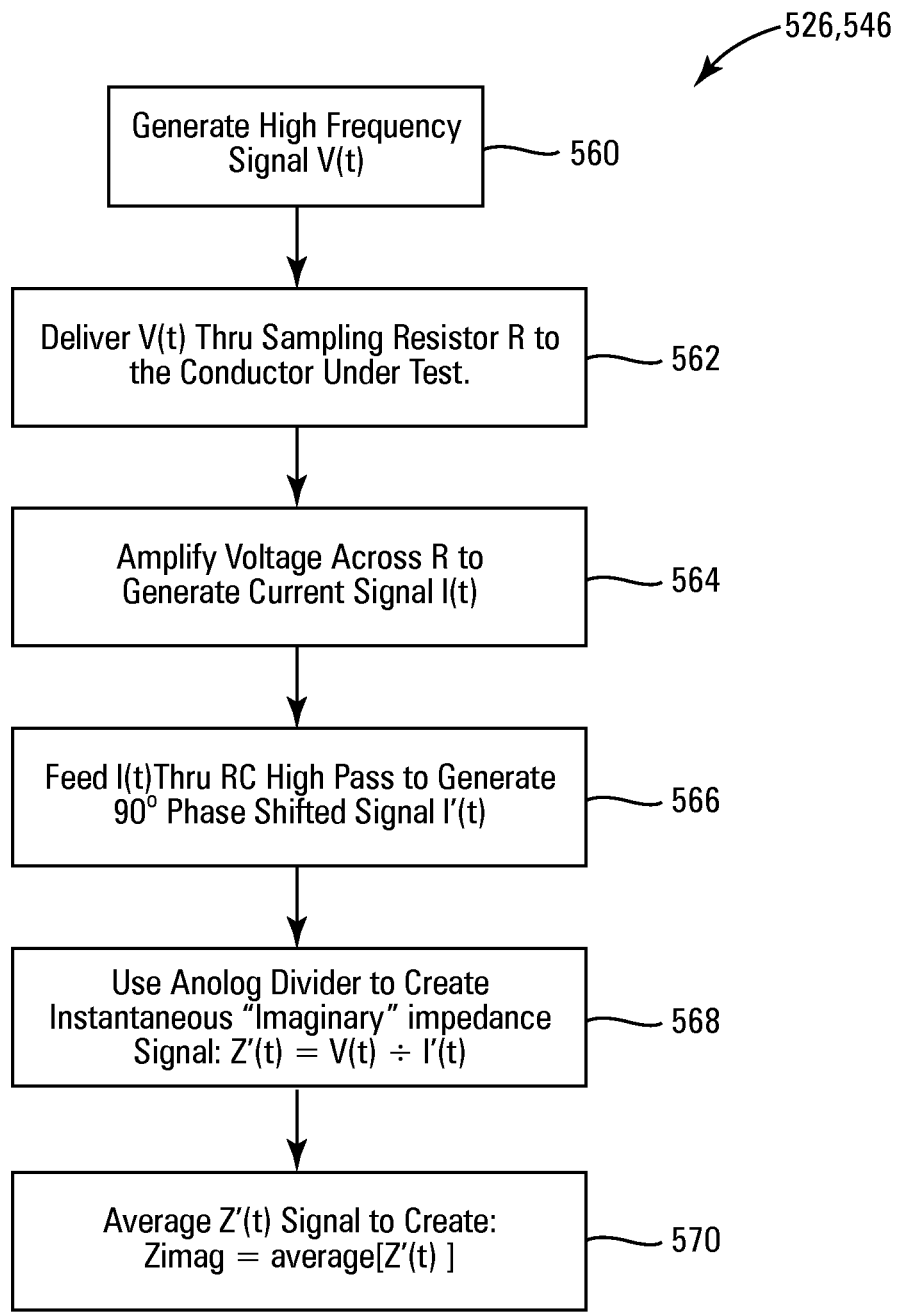
FIG. 59 is a flowchart illustrating a method for determining imaginary impedance according to an embodiment.

FIG. 59 is a flowchart illustrating a method for determining imaginary impedance 526, 546, as in FIGS. 57 and 58, according to an embodiment in which initial high frequency test signals 560 are generated from within the implantable pulse generator via special testing apparatus 50, as depicted, for example, in FIG. 16. Deliver the high frequency test signal through the sampling resistor to the conductor that is being tested occurs at 562. At 564, the voltage across the resistor is amplified to generate a testing current signal. The testing current signal is then fed through the high pass filter at 566 to generate a 90 degree phase shifted signal. An analog divider is then used to create an instantaneous "imaginary" impedance signal by dividing the high frequency signal by the phase shifted signal 568. The "imaginary" impedance is averaged at 570 by a processor or circuitry within the implantable pulse generator to create $Z_{imag}$. It will be understood that a similar process may be used to generate a value for $Z_{real}$ (slightly easier since no phase shift is required) and that a processor or circuitry within the implantable pulse generator may be programmed to automatically perform the analysis of these values, or may, instead, merely report out the raw values for analysis and consideration by the clinic. In various embodiments, the reporting out may comprise alert signals, periodic RF communications, or even communications linked over a remote communication system such as through the Internet to a clinic or physician.

Figure 60:
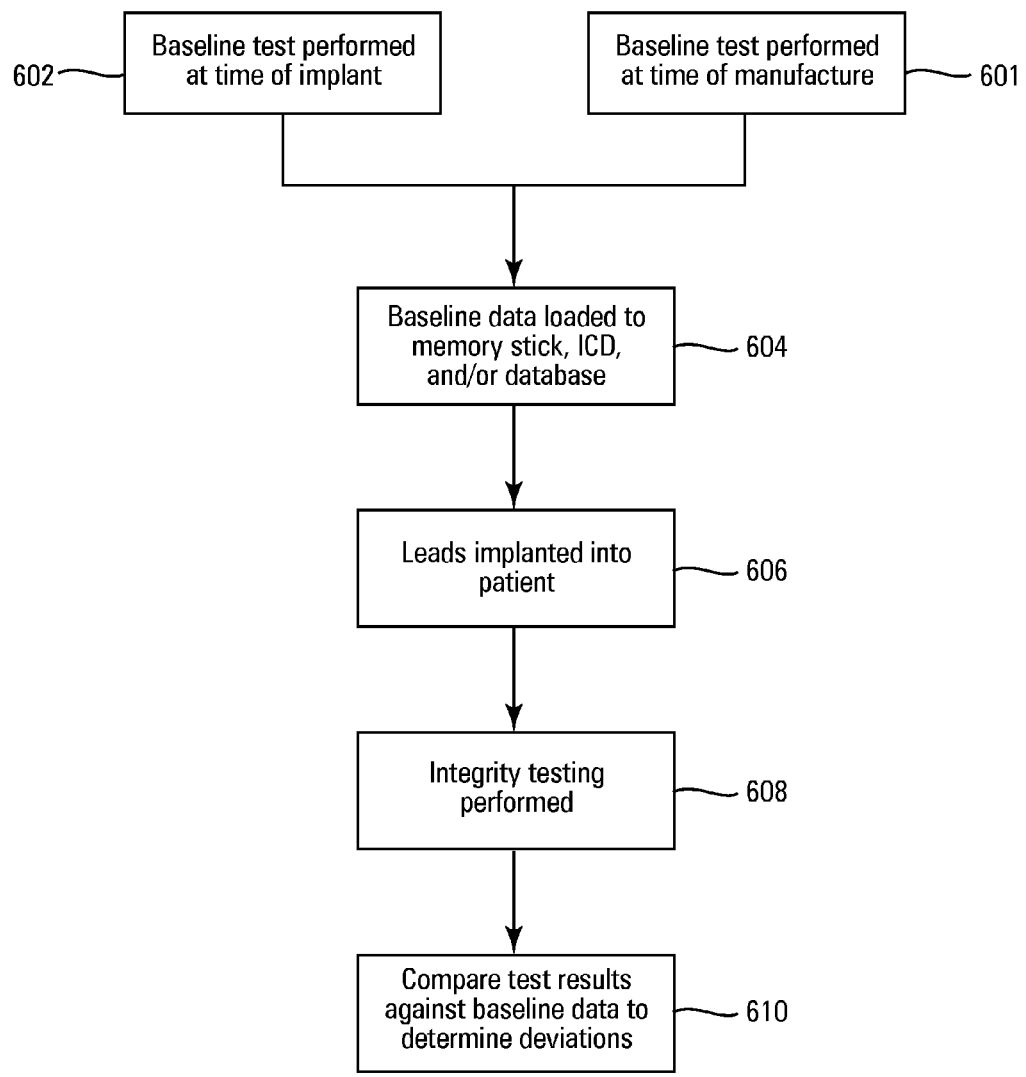
FIG. 60 depicts a method of baseline testing the leads at time of manufacture or at time of implant.

In an embodiment, as depicted in FIG. 60, a baseline test can be performed on the leads at the time of manufacture 601 or at the time of implant 602 to better refine the target frequencies for the test signals. The baseline data can be loaded on a memory stick, a chip within the ICD and/or loaded to a database 604. The leads are implanted into the patient 606 and may be further tested at this point. After implantation, the programmer reads the baseline data and performs integrity testing 608 on the lead comparing the results with the saved target frequencies 610. The baseline data refines and simplifies the imaginary testing since the target frequencies have already been generated. Thus, a standard is provided to measure deviations against and the implanted defibrillator does not have to sweep a large number of frequencies. An additional advantage is that power in the battery-powered implanted defibrillator can be saved due to the limited number of sweeps needing to be performed.

The values noted above are example embodiments and should not be read as limiting the scope of this invention. Those skilled in the art will recognize that the above values may be adjusted to practice the invention as necessary depending on the electrode implantable cardiac lead technology used and the physical characteristics of the patient.

While the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

The following application, the disclosure of which is incorporated by reference (other than claims and express definitions), is a prior art attempt by common inventors to solve the problem at issue: U.S. Publication No. 2014/0155947 to Kroll et al.

The invention claimed is:

1. A method to determine the integrity of an implantable cardiac lead implanted in a patient, comprising:
   determining a length of the implantable cardiac lead;
   calculating a test frequency based on the length;
   using a frequency signal source to apply a set of test signals to the implantable cardiac lead at frequencies within a predetermined range of the test frequency, each test signal including a phase shifted signal;
   measuring an instantaneous imaginary component of a transmission line impedance of the implantable cardiac lead in response to the each test signal;
   determining an imaginary impedance for each test signal based on the imaginary component of the transmission line impedance;
   comparing changes in the imaginary impedance for each test signal to a predetermined threshold to determine whether the implantable cardiac lead has a potential lead integrity issue; and
   communicating an indication of the potential lead integrity issue in response to determining that the implantable cardiac lead has a potential lead integrity issue by reporting the potential lead integrity issue for the patient to a medical professional.

2. The method of claim 1 wherein the method further comprises:
   extracting the implantable cardiac lead based upon determination of the potential lead integrity issue.

3. The method of claim 1 wherein:
   using the frequency signal source to apply the set of test signals includes generating a high frequency signal and delivering the high frequency signal across a sampling resistor to a selected conductor in the implantable cardiac lead;
   measuring the instantaneous imaginary component of the transmission line impedance includes amplifying a voltage across the sampling resistor to generate a current signal, generating a phase shifted signal from the current signal, and using an analog divider to create an instantaneous imaginary impedance value; and
   determining an imaginary impedance for each test signal includes repeating the using the frequency signal source and measuring the imaginary component for each of the set of test signals at a frequency unique to that test signal and within the predetermined range of the test frequency to obtain multiple instantaneous imaginary impedance values for each test signal and averaging the multiple instantaneous imaginary impedance values as the imaginary impedance for the selected conductor for that test signal.

4. The method of claim 1 wherein the predetermined range of the test frequency is +/−ten percent (10%) of the test frequency.

5. The method of claim 1 wherein the predetermined threshold is whether the imaginary impedance of any test signal varies by more than +/−ninety percent (90%) from an average imaginary impedance.

6. The method of claim 1 wherein the test frequency is greater than 100 MHz.

7. The method of claim 1 wherein the test frequency is in a range between 150 to 250 MHz.

8. The method of claim 7 wherein the test frequency is in a range between 170 to 200 MHz.

9. The method of claim 7 wherein the test frequency is in a range between 190 to 220 MHz.

10. The method of claim 1, wherein the indication of the potential lead integrity issue is communicated via at least one of: an alert signal, a periodic RF communication, or a remote communication system.

* * * * *